US012559553B2

(12) United States Patent
Billin et al.

(10) Patent No.: US 12,559,553 B2
(45) Date of Patent: Feb. 24, 2026

(54) IL-31 MODULATORS FOR TREATING FXR-INDUCED PRURITUS

(71) Applicant: Gilead Sciences, Inc., Foster City, CA (US)

(72) Inventors: Andrew Nicholas Billin, San Mateo, CA (US); Jun Xu, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 819 days.

(21) Appl. No.: 17/843,232

(22) Filed: Jun. 17, 2022

(65) Prior Publication Data

US 2023/0028715 A1 Jan. 26, 2023

Related U.S. Application Data

(60) Provisional application No. 63/251,533, filed on Oct. 1, 2021, provisional application No. 63/212,563, filed on Jun. 18, 2021.

(51) Int. Cl.
*C07K 16/24* (2006.01)
*A61P 17/04* (2006.01)

(52) U.S. Cl.
CPC ............ *C07K 16/244* (2013.01); *A61P 17/04* (2018.01)

(58) Field of Classification Search
CPC .......... A61P 17/04; A61P 29/00; A61P 37/08; C07K 16/244; C07K 16/2866; C07K 2317/76
See application file for complete search history.

(56) References Cited

U.S. PATENT DOCUMENTS

| | | | |
|---|---|---|---|
| 9,139,539 B2 | 9/2015 | Kinzel et al. | |
| 9,539,244 B2 | 1/2017 | Kinzel et al. | |
| 9,820,979 B2 | 11/2017 | Kinzel et al. | |
| 10,220,027 B2 | 3/2019 | Kinzel et al. | |
| 10,421,730 B2 | 9/2019 | Blomgren et al. | |
| 10,485,795 B2 | 11/2019 | Kinzel et al. | |
| 10,774,054 B2 | 9/2020 | Blomgren et al. | |
| 10,981,881 B2 | 4/2021 | Blomgren et al. | |
| 11,225,473 B2 | 1/2022 | Blomgren et al. | |
| 11,739,065 B2 | 8/2023 | Blomgren et al. | |
| 2020/0071282 A1* | 3/2020 | Blomgren | C07C 39/28 |
| 2025/0026744 A1 | 1/2025 | Blomgren et al. | |

FOREIGN PATENT DOCUMENTS

| | | | |
|---|---|---|---|
| CA | 3074034 A1 * | 5/2019 | A61K 1/506 |
| EP | 4019546 A1 | 6/2022 | |
| WO | WO-2016203347 A1 * | 12/2016 | A61K 31/4985 |

OTHER PUBLICATIONS

"Kulkarni AV et al, Efficacy and safety of obeticholic acid in liver disease-A systematic review and meta-analysis, Clin Res Hepatol Gastroenterol;45(3):101675, May 2021, Epub Mar. 17, 2021" (Year: 2021).*

"Kenji Kabashima et al, Interleukin-31 as a Clinical Target for Pruritus Treatment, Feb. 12, 2021, Frontiers in Medicine, 1-10" (Year: 2021).*

"Prasant Kumar Jena et al, Long-term Western diet intake leads to dysregulated bile acid signaling and dermatitis with Th2 and Th17 pathway features in mice, Jul. 2019, Journal of Dermatological Science, 13-20" (Year: 2019).*

Fiorucci S et al, Bile acid modulators for the treatment of nonalcoholic steatohepatitis (NASH), Jun. 19, 2020, Expert Opin Investig Drugs, 623-632 (Year: 2020).*

Farnesoid X receptor (FXR) activation and FXR genetic variation in inflammatory bowel disease, Nijmeijer RM et al., PLoS One, 2011;6(8):e23745, Epub Aug. 22, 2011 (Year: 2011).*

Xu et al. "FXR Agonism Elevates Circulating Levles of the Pruritogenic Cytokine IL-31" Nov. 2021, 2 pages, Conference Reports for NATAP [retrieved Sep. 26, 2025] Retrieved from the Internet: < https://www.natap.org/2021/AASLD/AASLD_117.htm > (Year: 2021).*

Arai, I. et al. Repeated administration of IL-31 upregulates IL-31 receptor A (IL-31RA) in dorsal root ganglia and causes severe itch-associated scratching behaviour in mice. Exp Dermatol. 2015;24(1):75-78.

Basile, F. et al. Interleukin 31 is involved in intrahepatic cholestasis of pregnancy. J Matern Fetal Neonatal Med. 2017;30(9):1124-1127.

Beuers, U. et al. Pruritus in cholestasis: facts and fiction. Hepatology. 2014;60(1):399-407.

Bieber, T. et al. Abrocitinib versus Placebo or Dupilumab for Atopic Dermatitis. N Engl J Med. 2021;384(12):1101-1112.

Castellani, M.L. et al. IL-31 a Th2 cytokine involved in immunity and inflammation. Int J Immunopathol Pharmacol. 2010;23(3):709-713.

Corpechot, C. et al. A Placebo-Controlled Trial of Bezafibrate in Primary Biliary Cholangitis. N Engl J Med. 2018;378(23):2171-2181.

De Vries, E. et al. Fibrates for Itch (FITCH) in Fibrosing Cholangiopathies: A Double-Blind, Randomized, Placebo-Controlled Trial. Gastroenterology. 2021; 160(3):734-743.e6.

Dillon, S.R. et al. Interleukin 31, a cytokine produced by activated T cells, induces dermatitis in mice. Nat Immunol. 2004;5(7):752-760.

Furue, M. et al. Emerging role of interleukin-31 and interleukin-31 receptor in pruritus in atopic dermatitis. Allergy. 2018;73(1):29-36.

Gonzales, A.J. et al. Interleukin-31: its role in canine pruritus and naturally occurring canine atopic dermatitis. Vet Dermatol. 2013;24(1):48-53, e11-42.

Kabashima, K. and Irie, H. Interleukin-31 as a Clinical Target for Pruritus Treatment. Front Med (Lausanne). 2021;8:638325.

Kabashima, K. et al. Trial of Nemolizumab and Topical Agents for Atopic Dermatitis with Pruritus. N Engl J Med. 2020;383(2):141-150.

(Continued)

*Primary Examiner* — Joanne Hama
(74) *Attorney, Agent, or Firm* — Sheppard Mullin Richter & Hampton LLP

(57) ABSTRACT

The present disclosure relates generally to methods of using modulators of interleukin-31 (IL-31) for treating, stabilizing, or lessening the severity or progression of pruritis.

7 Claims, 11 Drawing Sheets

(56) References Cited

OTHER PUBLICATIONS

Kowdley, K.V. et al. The Nonsteroidal Farnesoid X Receptor (FXR) Agonist Cilofexor Improves Liver Biochemistry in Patients with Primary Biliary Cholangitis (PBC): A Phase 2, Randomized, Placebo-Controlled Trial. Hepatology. 2019;70(suppl. 1):31a-32a.
Kremer, A.E. et al. Lysophosphatidic acid is a potential mediator of cholestatic pruritus. Gastroenterology. 2010;139(3):1008-1018, 1018.e1.
Kremer, A.E. et al. Pathophysiology and current management of pruritus in liver disease. Clin Res Hepatol Gastroenterol. 2011;35(2):89-97.
Kremer, A.E. et al. Seladelpar treatment reduces IL-31 and pruritus in patients with primary biliary cholangitis. Hepatology. 2024;80(1):27-37.
Lu, J. et al. Serum interleukin-31 level and pruritus in atopic dermatitis: A Meta-analysis. Zhong Nan Da Xue Xue Bao Yi Xue Ban. 2018;43(2):124-130.
Mu, N. et al. Implication of Increased Serum IL-31 for Primary Biliary Cholangitis. Immunol Invest. 2020:1-9.
Oyama, S. et al. Cynomolgus monkey model of interleukin-31-induced scratching depicts blockade of human interleukin-31 receptor A by a humanized monoclonal antibody. Exp Dermatol. 2018;27(1):14-21.
Patel, K. et al. Cilofexor, a Nonsteroidal FXR Agonist, in Patients With Noncirrhotic Nash: A Phase 2 Randomized Controlled Trial. Hepatology. 2020;72(1):58-71.
Ruzicka, T. et al. Anti-Interleukin-31 Receptor A Antibody for Atopic Dermatitis. N Engl J Med. 2017;376(9):826-835.
Schwabl, P. et al. The Non-Steroidal FXR Agonist Cilofexor Improves Portal Hypertension and Reduces Hepatic Fibrosis in a Rat NASH Model. Biomedicines. 2021;9(1):60.
Stott, B. et al. Human IL-31 is induced by IL-4 and promotes TH2-driven inflammation. J Allergy Clin Immunol. 2013;132(2):446-454.e5.
Trauner, M. et al. The Nonsteroidal Farnesoid X Receptor Agonist Cilofexor (GS-9674) Improves Markers of Cholestasis and Liver Injury in Patients With Primary Sclerosing Cholangitis. Hepatology. 2019;70(3):788-801.
Trivedi, H. et al. Management of Pruritus in Primary Biliary Cholangitis: A Narrative Review. Am J Med. 2017; 130(6):744.e1-744.e7.
Tseng, P.Y. and Hoon, M.A. Oncostatin M can sensitize sensory neurons in inflammatory pruritus. Sci Transl Med. 2021;13(619):eabe3037.
Xu, J. et al. IL-31 levels correlate with pruritus in patients with cholestatic and metabolic liver diseases and is farnesoid X receptor responsive in NASH. Hepatology. 2023;77(1):20-32.
Yu, H. et al. MRGPRX4 is a bile acid receptor for human cholestatic itch. Elife. 2019;8:e48431.
Yu, X. et al. The Transforming Growth Factor β1/Interleukin-31 Pathway Is Upregulated in Patients with Hepatitis B Virus-Related Acute-on-Chronic Liver Failure and Is Associated with Disease Severity and Survival. Clin Vaccine Immunol. 2015;22(5):484-492.
Zhang, Q. et al. Structures and biological functions of IL-31 and IL-31 receptors. Cytokine Growth Factor Rev. 2008;19(5-6):347-56.
International Search Report and Written Opinion, dated Oct. 17, 2022, regarding International Application No. PCT/US2022/033997, 10 pages.
Datsi et al., Interleukin-31: The 'itchy' cytokine in inflammation and therapy, Nov. 27, 2020, https://d197for5662m48.cloudfront.net/documents/publicationstatus/53681/preprint_pdf/9827b3d5405f3c9e0fc74f5895817f60. pdf.

* cited by examiner

IL-31 MODULATORS FOR TREATING FXR-INDUCED PRURITUS

CROSS-REFERENCE TO RELATED APPLICATIONS

This application claims benefit to U.S. Provisional Patent Application No. 63/212,563, filed Jun. 18, 2021, and U.S. Provisional Patent Application No. 63/251,533, filed Oct. 1, 2021. The contents of each of the aforementioned applications are incorporated by reference herein in their entireties.

FIELD

The present disclosure relates generally to methods of using modulators of interleukin-31 (IL-31) for treating, stabilizing, or lessening the severity or progression of pruritus.

BACKGROUND

The Farnesoid X Receptor (FXR), also often referred to as NR1H4 (nuclear receptor subfamily 1, group H, member 4) when referring to the human receptor, is a nuclear hormone receptor. FXR has been associated with multiple biological functions. FXR is primarily expressed in the liver and throughout the entire gastrointestinal tract, but is also found in the kidney, adrenal glands, and ovary. FXR is associated with controlling intracellular gene expression, and may be involved in paracrine and endocrine signaling. In the intestine and liver, FXR functions as a regulator of bile acid homeostasis and hepatic lipogenesis. FXR has also been associated with Kupffer cells and liver sinusoidal endothelial cells of the liver, wherein it is believed to have functions related to inflammation, fibrosis, and portal hypertension.

A number of FXR agonists are known and are being investigated in connection with a number of physiological conditions, including liver diseases. FXR agonists can have benefits in steatosis, lobular inflammation, hepatocellular ballooning, and fibrosis.

FXR agonism can lead to different effects in different regions in the body. In the distal small intestine and systemically in organs such as the liver, activation of FXR directly causes the expression and secretion of the hormone, FGF19. FGF19 modulates bile acid (BA) by down regulating bile acid synthesis, which can be beneficial, for example, in conditions such as liver disease.

While FXR agonists have also been associated with adverse effects, such as pruritus, the causative pruritogen was unknown heretofore.

SUMMARY

It is contemplated herein that interleukin-31 (IL-31) is a putative biomarker for pruritus associated with FXR agonism. IL-31 is a member of the IL-6 family of cytokines and acts as a ligand for IL-31 receptor A (IL-31RA) and oncostatin M receptor (OSMR) heterodimer. Activation of the IL-31 receptor transduces intracellular signaling through Janus kinase (JAK) and phosphorylation of STAT transcription factors.

Provided herein are methods of treating Farnesoid X Receptor (FXR)-induced pruritus comprising administering to a patient in need thereof an effective amount of an agent that inhibits interleukin-31 (IL-31).

Provided herein are methods of treating Farnesoid X Receptor (FXR)-induced pruritus comprising administering to a patient in need thereof an effective amount of an agent that inhibits Janus kinase (JAK).

Some embodiments provide for methods of treating pruritus associated with chronic cholestatic liver disease, comprising administering to a patient in need thereof an effective amount of an agent that inhibits IL-31.

Some embodiments provide for methods of treating pruritus comprising administering to a patient in need thereof an effective amount of an agent that inhibits IL-31, wherein the pruritus is due to the patient being administered an FXR agonist or the pruritus is associated with elevated serum IL-31 levels due to increased serum bile acid levels.

Some embodiments provide for methods for treating FXR-induced pruritus comprising administering to a patient in need thereof an effective amount of an FXR agonist and an effective amount of an agent that inhibits IL-31.

Also provided herein are methods for treating FXR-induced pruritus comprising administering to the patient a means for inhibiting IL-31.

Also provided herein are methods for treating FXR-induced pruritus comprising administering to the patient a means for inhibiting JAK.

Also provided herein are methods for treating FXR-induced pruritus comprising administering to the patient a means for slowing or preventing an increase in serum IL-31 levels.

Also provided herein are compositions comprising an FXR agonist and a means for inhibiting IL-31 or a means for slowing or preventing an increase in serum IL-31 levels.

Also provided herein are compositions comprising an FXR agonist and a means for inhibiting JAK.

DETAILED DESCRIPTION

Definitions and General Parameters

Figure 1A:
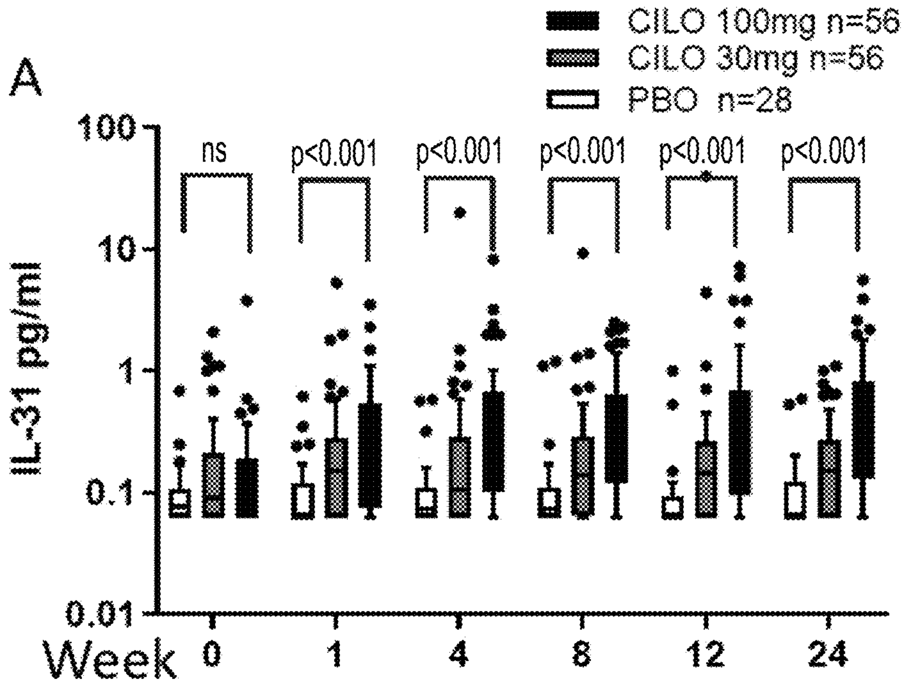
FIG. 1A and FIG. 1B show serum IL-31 levels in non-alcoholic steatohepatitis (NASH) patients treated with cilofexor (CILO) for 24 weeks.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

As used herein generally, "agent which inhibits interleukin-31" or "compound which inhibits IL-31" or "agent that inhibits interleukin-31" or "compound that inhibits IL-31" means any therapeutic agent that reduces the activity of IL-31 (interleukin-31). In some embodiments, "agent which inhibits interleukin-31" or "compound which inhibits IL-31" or "agent that inhibits interleukin-31" or "compound that inhibits IL-31" means any therapeutic agent that reduces IL-31 (interleukin-31) signaling. The therapeutic agent that reduces the IL-31 signaling may be via interaction with IL-31 ligand or via interaction with an IL-31 receptor. The receptor for IL-31 is a heterodimeric complex that is composed of IL-31 receptor A ("IL-31RA") and the oncostatin M receptor ("OSMR"). Thus, an "agent which inhibits interleukin-31" or "compound which inhibits IL-31" or "agent that inhibits interleukin-31" or "compound that inhibits IL-31" may refer to an agent targeting IL-31, or an agent targeting IL-31RA, or an agent targeting OSMR.

As used herein generally, "agent which inhibits janus kinase (JAK)" or "compound which inhibits JAK" or "agent that inhibits janus kinase (JAK)" or "compound that inhibits JAK" means any therapeutic agent that reduces the activity of a janus kinase (JAK1, JAK2, JAK3, or TYK2).

As used herein, a "FXR agonist" refers to any agent that is capable of binding and activating farnesoid X receptor (FXR) which may be referred to as bile acid receptor (BAR) or NR1H4 (nuclear receptor subfamily 1, group H, member 4) receptor. FXR agonist may act as agonists or partial agonists of FXR. The agent may be a chemical compound or biological molecule (e.g., a protein or antibody).

As used herein generally, "ACC inhibitor" or "ACCi" means any therapeutic agent that reduces the activity of an acetyl CoA carboxylase enzyme.

As used herein, the term "Farnesoid X Receptor (FXR)-induced pruritus" or "FXR-induced pruritus" refers to pruritus brought about by FXR activation. In some embodiments, the FXR-induced pruritus is due to the patient being administered an FXR agonist. In some embodiments, the FXR-induced pruritus is associated with elevated serum IL-31 levels due to increased serum bile acid levels.

The term "inhibition" indicates a decrease in the baseline activity of a biological activity or process. "Inhibition of activity of IL-31" or "inhibition of JAK" or variants thereof refers to a decrease in activity in IL-31 or JAK as a direct or indirect response to the presence of a compound described herein relative to the activity of IL-31 or JAK in the absence of the compound described herein. In some embodiments, the inhibition of IL-31 or JAK activity may be compared in the same subject prior to treatment, or other subjects not receiving the treatment.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, or lessening the severity or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

As used herein, the term "subject" refers to a mammalian subject. Exemplary subjects include, but are not limited to humans, monkeys, dogs, cats, mice, rats, cows, horses, goats and sheep. In some embodiments, the subject is human.

A "pharmaceutical composition" is intended to include the combination of an active agent with a carrier, inert or active, making the composition suitable for diagnostic or therapeutic use in vitro, in vivo or ex vivo.

The term "therapeutically effective amount" or "effective amount" of a compound described herein or a pharmaceutically acceptable salt, tautomer, stereoisomer, mixture of stereoisomers, prodrug, or deuterated analog thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of IL-31 activity or JAK activity. The therapeutically effective amount may vary depending on the subject, and disease or condition being treated, the weight and age of the subject, the severity of the disease or condition, and the manner of administering, which can readily be determined by one or ordinary skill in the art.

A dash ("—") that is not between two letters or symbols is used to indicate a point of attachment for a substituent. For example, $-C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art. Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. $-(CH_2)_3CH_3$), sec-butyl (i.e. $-CH(CH_3)CH_2CH_3$), isobutyl (i.e. $-CH_2CH(CH_3)_2$) and tert-butyl (i.e. $-C(CH_3)_3$); and "propyl" includes n-propyl (i.e. $-(CH_2)_2CH_3$) and isopropyl (i.e. $-CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, and butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group $-C(O)NR^yR^z$ and an "N-amido" group which refers to the group $-NR^yC(O)R^z$, wherein $R^y$ and $R^z$ are independently selected from the group consisting of hydrogen, alkyl, aryl, haloalkyl, or heteroaryl; each of which may be optionally substituted.

"Amino" refers to the group $-NR^yR^z$ wherein $R^y$ and $R^z$ are independently selected from the group consisting of hydrogen, alkyl, haloalkyl, aryl, or heteroaryl; each of which may be optionally substituted.

"Amidino" refers to $-C(NH)(NH_2)$.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthylenyl, fluorenyl, and anthracenyl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to $-N_3$.

"Carbamoyl" refers to both an "O-carbamoyl" group which refers to the group $-O-C(O)NR^yR^z$ and an "N-carbamoyl" group which refers to the group $-NR^yC(O)OR^z$, wherein $R^y$ and $R^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Guanidino" refers to $-NHC(NH)(NH_2)$.

"Hydrazino" refers to $-NHNH_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl ($-CHF_2$) and trifluoromethyl ($-CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, $-S(O)_2-$, and the like, where R is H, alkyl, aryl, cycloalkyl, heteroalkyl, heteroaryl or heterocyclyl, each of which may be optionally substituted. Examples of heteroalkyl groups include $-OCH_3$, $-CH_2OCH_3$, $-SCH_3$, $-CH_2SCH_3$, $-NRCH_3$, and $-CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo [1,5-a]pyridinyl, where the heteroaryl can be bound via either ring of the fused system. Any aromatic ring, having a single ring or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Oxo" refers to the group (═O) or (O).

"Nitro" refers to the group $—NO_2$.

"Alkylsulfonyl" refers to the group $—S(O)_2R$, where R is alkyl.

"Alkylsulfinyl" refers to the group —S(O)R, where R is alkyl.

"Thiocyanate" —SCN.

"Thiol" refers to the group —SR, where R is alkyl, haloalkyl, heterocyclyl, cycloalkyl, heteroaryl, or aryl.

"Thioxo" or "thione" refer to the group (═S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last-mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated, are provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds as described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound as described herein when administered to a mammal, such as a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound as described herein.

The concentration of such a heavier isotope, specifically deuterium, may be defined by an isotopic enrichment factor. In the compounds of this disclosure any atom not specifically designated as a certain isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In some cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

A "solvate" is formed by the interaction of a solvent and a compound. Solvates of salts of the compounds described herein are also provided. Hydrates of the compounds described herein are also provided.

Methods

Farnesoid X receptor (FXR) is a nuclear hormone receptor expressed in the intestinal epithelial cells and hepatocytes, and functions as an enterohepatic regulator of bile acid homeostasis. Activation of FXR in the intestinal epithelial cell results in elevated expression and secretion of endocrine FGF-19 into enterohepatic circulation. FGF-19 binds to its cognate receptor FGFR4/0-Klotho receptor complex on hepatocyte and induces expression of small heterodimer partner (SHP), which represses expression of CYP7A1, the rate-limiting enzyme for bile acid (BA) synthesis. BA is the natural ligand for FXR and physiological activation of FXR in hepatocyte or through FGF-19 released from intestinal epithelial cells negatively regulates BA homeostasis.

FXR agonist demonstrated a positive result of improved cholestasis or liver fibrosis in PBC, PSC, and NASH patients. Pruritus is not typically noted in NASH patients, but increased pruritus is a common adverse event for FXR agonists. The pruritogen was unknown heretofore.

It is contemplated herein that IL-31 is a putative biomarker for pruritus associated with FXR agonism. IL-31 is a member of the IL-6 family of cytokines and acts as a ligand for IL-31 receptor A (IL-31RA) and oncostatin M receptor (OSMR) heterodimer. Activation of the IL-31 receptor transduces intracellular signaling through Janus kinase (JAK) and phosphorylation of STAT transcription factors.

Provided herein are methods of treating Farnesoid X Receptor (FXR)-induced pruritus comprising administering to patient in need thereof an effective amount of an agent that inhibits interleukin-31 (IL-31).

Also provided herein are methods of treating Farnesoid X Receptor (FXR)-induced pruritus comprising administering to patient in need thereof an effective amount of an agent that inhibits Janus kinase (JAK).

In some embodiments, the FXR-induced pruritus is due to the patient being administered an FXR agonist. The FXR agonist may be an FXR agonist as described herein. In some embodiments, the FXR-induced pruritus is due to the patient being administered cilofexor.

In some embodiments, the FXR-induced pruritus is associated with elevated serum IL-31 levels. In some embodiments, the elevated serum IL-31 levels is due to increased levels of natural ligands of FXR. In some embodiments, the natural ligand is bile acid due to increased serum bile acid levels or farnesol.

In some embodiments, the FXR-induced pruritus is associated with elevated serum IL-31 levels due to increased serum bile acid levels.

Some embodiments provide for methods of treating pruritus associated with chronic cholestatic liver disease, comprising administering to a patient in need thereof an effective amount of an agent that inhibits IL-31.

Some embodiments provide for methods of treating pruritus associated with chronic cholestatic liver disease, comprising administering to a patient in need thereof an effective amount of an agent that inhibits JAK.

In some embodiments, the chronic cholestatic liver disease is PBC or PSC.

Some embodiments provide for methods of treating pruritus comprising administering to a patient in need thereof an effective amount of an agent that inhibits IL-31, wherein the pruritus is due to the patient being administered an FXR agonist or the pruritus is associated with elevated serum IL-31 levels due to increased serum bile acid levels.

In some embodiments, the pruritus is due to the patient being administered an FXR agonist. In some embodiments, the pruritus is due to the patient being administered cilofexor.

In some embodiments, the pruritus is associated with elevated serum IL-31 levels due to increased serum bile acid levels.

In some embodiments, the agent that inhibits IL-31 is an antibody that blocks signaling of IL-31. In some embodiments, the agent that inhibits IL-31 is an anti-IL31 antibody, an anti-IL-31RA antibody, or an anti-oncostatin M receptor beta antibody. In some embodiments, the agent that inhibits IL-31 is nemolizumab, BMS-981164, or KPL-716. In some embodiments, the agent that inhibits IL-31 is lokivetmab, vixarelimab (KPL-716), nemolizumab, BMS-981164, or a combination thereof.

In some embodiments, the agent that inhibits IL-31 is lokivetmab. Lokivetmab is a caninized monoclonal antibody that specifically targets IL-31.

In some embodiments, the agent that inhibits IL-31 is vixarelimab. Vixarelimab is a fully-human monoclonal antibody that targets oncostatin M receptor beta, thereby mediating both IL-31 and oncostatin M.

In some embodiments, the agent that inhibits IL-31 is nemolizumab. Nemolizumab is a humanized monoclonal antibody that targets IL-31 receptor A.

In some embodiments, the agent that inhibits IL-31 is BMS-981164. BMS-981164 is a monoclonal antibody that targets IL-31.

In some embodiments, methods described herein further comprise administering an effective amount of an agent that inhibits janus kinase (JAK).

Some embodiments provide for methods of treating pruritus comprising administering to a patient in need thereof an effective amount of an agent that inhibits JAK, wherein the pruritus is due to the patient being administered an FXR agonist or the pruritus is associated with elevated serum IL-31 levels due to increased serum bile acid levels.

In some embodiments, the pruritus is due to the patient being administered an FXR agonist. In some embodiments, the pruritus is due to the patient being administered cilofexor.

In some embodiments, the pruritus is associated with elevated serum IL-31 levels due to increased serum bile acid levels.

In some embodiments, the agent that inhibits JAK is selected from: a TYK2 inhibitor, BMS-986165, brepocitinib (PF-06700841), TD-1473, OST-122, BMS-986322, NDI-031301, delgocitinib, fedratinib, peficitinib, panobinostat, izencitinib, momelotinib, deucravacitinib, itacitinib, SHR-0302, deuroxolitinib, ritlecitinib, jaktinib, ARQ-252, pacritinib, CEP-33779, decernotinib, oclacitinib, filgotinib, baricitinib, ruxolitinib, tofacitinib, upadacitinib, abrocitinib, or a pharmaceutically acceptable salt thereof, and a combination thereof. In some embodiments, the agent that inhibits JAK is tofacitinib. In some embodiments, the agent that inhibits JAK is filgotinib. In some embodiments, the agent that inhibits JAK is baricitinib.

Provided herein are methods for treating FXR-induced pruritus comprising administering to a patient in need thereof an effective amount of an FXR agonist and an effective amount of an agent that inhibits IL-31.

In some embodiments, the patient is administered an FXR agonist and an agent that inhibits IL-31 sequentially (i.e. in separate forms and at separate times). In some embodiments, the patient is administered an FXR agonist and an agent that inhibits IL-31 concurrently. In such embodiments, the FXR agonist can be submitted as separate forms or the same form (i.e. in composition as described herein).

In some embodiments, the patient is administered an FXR agonist prior to administration of the agent that inhibits IL-31.

Also provided herein are methods for treating FXR-induced pruritus comprising administering to a patient in need thereof an effective amount of an FXR agonist and an effective amount of an agent that inhibits JAK. In some embodiments, the patient is administered an FXR agonist and an agent that inhibits JAK sequentially. In some embodiments, the patient is administered an FXR agonist and an agent that inhibits JAK concurrently. In some embodiments, the patient is administered an FXR agonist prior to administration of the agent that inhibits JAK.

Also provided herein are methods for treating FXR-induced pruritus comprising administering to a patient in need thereof an effective amount of an FXR agonist, an effective amount of an agent that inhibits IL-31, and an effective amount of an agent that inhibits JAK. In some embodiments, the patient is administered an FXR agonist prior to administration of the agent that inhibits IL-31. In some embodiments, the patient is administered an FXR agonist prior to administration of the agent that inhibits JAK. In some embodiments, the patient is administered an FXR agonist prior to administration of the agent that inhibits IL-31 and the agent that inhibits JAK.

Provided herein are methods for treating FXR-induced pruritus comprising administering to a patient in need thereof an effective amount of cilofexor and an effective amount of an agent that inhibits IL-31. In some embodiments, the patient is administered cilofexor prior to administration of the agent that inhibits IL-31.

Also provided herein are methods for treating FXR-induced pruritus comprising administering to a patient in need thereof an effective amount of cilofexor and an effective amount of an agent that inhibits JAK. In some embodiments, the patient is administered cilofexor prior to administration of the agent that inhibits JAK.

Also provided herein are methods for treating FXR-induced pruritus comprising administering to a patient in need thereof an effective amount of cilofexor, an effective amount of an agent that inhibits IL-31, and an effective amount of an agent that inhibits JAK. In some embodiments, the patient is administered cilofexor prior to administration of the agent that inhibits IL-31. In some embodiments, the patient is administered cilofexor prior to administration of the agent that inhibits JAK. In some embodiments, the patient is administered cilofexor prior to administration of the agent that inhibits IL-31 and the agent that inhibits JAK.

Provided herein are methods for treating pruritus comprising administering to a patient in need thereof an effective amount of an FXR agonist and an effective amount of an agent that inhibits IL-31. In some embodiments, the patient is administered an FXR agonist prior to administration of the agent that inhibits IL-31.

Also provided herein are methods for treating pruritus comprising administering to a patient in need thereof an effective amount of an FXR agonist and an effective amount of an agent that inhibits JAK. In some embodiments, the patient is administered an FXR agonist prior to administration of the agent that inhibits JAK.

Also provided herein are methods for treating pruritus comprising administering to a patient in need thereof an effective amount of an FXR agonist, an effective amount of an agent that inhibits IL-31, and an effective amount of an agent that inhibits JAK. In some embodiments, the patient is administered an FXR agonist prior to administration of the agent that inhibits IL-31. In some embodiments, the patient is administered an FXR agonist prior to administration of the agent that inhibits JAK. In some embodiments, the patient is administered an FXR agonist prior to administration of the agent that inhibits IL-31 and the agent that inhibits JAK.

In some embodiments, the pruritus is due to the patient being administered an FXR agonist or the pruritus is associated with elevated serum IL-31 levels due to increased serum bile acid levels.

Provided herein are methods for treating pruritus comprising administering to a patient in need thereof an effective amount of cilofexor and an effective amount of an agent that inhibits IL-31. In some embodiments, the patient is administered cilofexor prior to administration of the agent that inhibits IL-31.

Also provided herein are methods for treating pruritus comprising administering to a patient in need thereof an effective amount of cilofexor and an effective amount of an agent that inhibits JAK. In some embodiments, the patient is administered cilofexor prior to administration of the agent that inhibits JAK.

Also provided herein are methods for treating pruritus comprising administering to a patient in need thereof an effective amount of cilofexor, an effective amount of an agent that inhibits IL-31, and an effective amount of an agent that inhibits JAK. In some embodiments, the patient is administered cilofexor prior to administration of the agent that inhibits IL-31. In some embodiments, the patient is administered cilofexor prior to administration of the agent that inhibits JAK. In some embodiments, the patient is administered cilofexor prior to administration of the agent that inhibits IL-31 and the agent that inhibits JAK.

In some embodiments, the pruritus is due to the patient being administered cilofexor. In some embodiments, the pruritus is associated with elevated serum IL-31 levels due to increased serum bile acid levels.

Provided herein are methods for treating FXR-induced pruritus comprising administering to the patient a means for inhibiting IL-31.

Also provided herein are methods for treating FXR-induced pruritus comprising administering to the patient a means for inhibiting JAK.

Provided herein are methods for treating FXR-induced pruritus comprising administering to the patient a means for slowing or preventing an increase in serum IL-31 levels.

It will be appreciated, in embodiments where the agent that inhibits IL-31 and/or the agent that inhibits JAK is administered with one or more additional therapeutic agents, the administration can occur on the same day or on different days and in any order as according to an appropriate dosing protocol.

In some embodiments, administration of an FXR agonist starts a period of time (as such at least one day, three days, one week, two weeks, or a month) before administration of an agent that inhibits IL-31, and optionally continues during at least part of the administration period of the agent that inhibits IL-31.

In some embodiments, administration of an FXR agonist starts a period of time (as such at least one day, three days, one week, two weeks, or a month) before administration of an agent that inhibits JAK, and optionally continues during at least part of the administration period of the agent that inhibits JAK.

In some embodiments, administration of an FXR agonist starts on the same day administration of an agent that inhibits IL-31 or an agent that inhibits JAK starts.

In some embodiments, an agent that inhibits IL-31 or an agent that inhibits JAK is administered with an FXR agonist for at least a period of time (as such at least one day, three days, one week, two weeks, or a month) after administration of the agent that inhibits IL-31 or the agent that inhibits JAK starts.

FXR Mediated Conditions

In some embodiments, the patient of the methods described herein is suffering from an FXR mediated condition. In some embodiments, the FXR mediated condition is: a chronic intrahepatic or form of extrahepatic cholestatic condition; liver fibrosis; an acute intraheptic cholestatic condition; an obstructive or chronic inflammatory disorder that arises out of improper bile composition; a gastrointestinal condition with a reduced uptake of dietary fat and fat-soluble dietary vitamins; inflammatory bowel diseases; lipid and lipoprotein disorders; Type II Diabetes and clinical complications of Type I and Type II Diabetes; a condition or disease which result from chronic fatty and fibrotic degeneration of organs due to enforced lipid and specifically triglyceride accumulation and subsequent activation of profibrotic pathways; obesity and metabolic syndrome (combined conditions of dyslipidemia, diabetes and abnormally high body-mass index); acute myocardial infarction; acute stroke; thrombosis which occurs as an endpoint of chronic obstructive atherosclerosis; persistent infections by intracellular bacteria or parasitic protozoae; non-malignant hyperproliferative disorders; malignant hyperproliferative disorders; colon adenocarcinoma and hepatocellular carcinoma; liver steatosis and associated syndromes; liver failure or liver malfunction as an outcome of chronic liver diseases or of surgical liver resection; Hepatitis B infection; Hepatitis C infection and/or cholestatic and fibrotic effects that are associated with alcohol-induced cirrhosis or with viral-borne forms of hepatitis.

FXR can modulate both the synthetic output of bile acids in the liver and their recycling in the intestine (by regulating bile acid binding proteins). FXR can be involved in the regulation of many diverse physiological processes that are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases, or chronic intrahepatic forms of cholestasis.

FXR regulates a complex pattern of response genes in the liver and in the gastrointestinal tract. The gene products have impact on diverse physiological processes. For example, FXR represses the induction of Cyp7A1 via the upregulation of mRNA encoding SHP, a further nuclear receptor that is dominant repressive over LRH-1. Since FXR binds primary bile acids, the end products of this pathway, this can be regarded as an example of feedback inhibition on the gene expression level.

FXR ligands induce bile flow and change bile acid composition towards more hydrophilic composition. With the development of the first synthetic FXR ligand GW4064 as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, hepatoprotective effects could also be demonstrated. These hepatoprotective effects included anti-fibrotic effects resulting from the repression of Tissue Inhibitors of Matrix-Metalloproteinases TIMP-1 and 2, the induction of collagen-deposit resolving Matrix-Metalloproteinase 2 in hepatic stellate cells, and the subsequent reduction of alpha-collagen mRNA and Transforming growth factor beta (TGF-beta) mRNA, both of which are pro-fibrotic factors.

Furthermore, anti-cholestatic activity was demonstrated in bile-duct ligated animal models as well as in animal models of estrogen-induced cholestasis. Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al., Gastroenterology 2004, 126, 756; L. Alvarez et al., Hum. Mol. Genet. 2004, 13, 2451) or levels of the FXR target gene encoding MDR-3 phospholipid export pump are reduced (in PFIC Type III). There is a growing body of evidence that FXR binding compounds can demonstrate substantial clinical utility in the therapeutic regimen of chronic cholestatic conditions such as Primary Biliary Cirrhosis (PBC) or Primary Sclerosing Cholangitis (PSC).

FXR agonists can be useful to prevent cholesterol gallstone formation or to prevent re-formation of gallstones after surgical removal or shockwave lithotripsy. For example, using the synthetic FXR tool compound GW4064 it could be demonstrated that activation of FXR leads to an improvement of the Cholesterol Saturation Index (CSI) and directly to an abolishment of gallstone formation in C57L gallstone susceptible mice whereas drug treatment in FXR knockout mice shows no effect on gallstone formation.

Thus, in one embodiment of the disclosure, an FXR mediated condition is an obstructive or chronic inflammatory disorder that arises out of improper bile composition such as cholelithiasis also known as cholesterol gallstones.

FXR agonists can be useful in protecting the intestine from neoplastic transformation and from the development of polyps and their transition into adenocarcinoma in the gut. Absence of FXR leads to a high increase in the formation of Hepatocellular Cacrcinoma (HCC), the most prominent form of liver cancer. Whereas a functional FXR prevents the formation of colon adenocarcinoma and hepatocellular carcinoma, FXR activation induces liver regeneration after hepatectomy.

The combined hepatoprotective, anti-neoplastic and liver regenerative effects associated with FXR activation can be therapeutically exploited for the use of FXR agonists in the treatment of severe liver diseases.

In one embodiment, the FXR mediated condition is a liver disease, such as HCC, stimulation of liver regrowth and amelioration of side effects associated with major liver resection, liver cirrhosis independent of the etiology and prevention or treatment of liver ischemia in the course of liver transplantation or major liver surgery.

Moreover, FXR can be a key regulator of serum triglycerides. Activation of FXR by synthetic agonists can leads to significant reduction of serum triglycerides, mainly in the form of reduced VLDL, but also to reduced total serum cholesterol. Lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment. An effect on reduction of body weight was also recently observed in mice overfed with a high lipid diet. This weight loss effect might result from FXR's induction of FGF-19, a fibroblast growth factor that is known to lead to weight loss and athletic phenotype. The effect of FXR agonist on reduction of body weight has been demonstrated.

Accordingly, FXR agonists can be exploited in different therapeutic ways: FXR binding compounds are thought to be good candidates for the treatment of Type II Diabetes because of their insulin sensitization, glycogenogenic, and lipid lowering effects.

In some embodiments, FXR mediated condition is Type II Diabetes which can be overcome by FXR-mediated upregulation of systemic insulin sensitivity and intracellular insulin signaling in liver, increased peripheral glucose uptake and metabolization, increased glycogen storage in liver, decreased output of glucose into serum from liver-borne gluconeogenesis.

In some embodiments, the FXR mediated condition is chronic intrahepatic, such as PBC, PSC, progressive familiar cholestasis (PFIC), alcohol-induced cirrhosis and associated cholestasis, and some forms of extrahepatic cholestatic conditions, or liver fibrosis.

In some embodiments, the FXR mediated condition is a gastrointestinal condition with a reduced uptake of dietary fat and fat-soluble dietary vitamins which can be overcome by increased intestinal levels of bile acids and phospholipids.

In some embodiments, the FXR mediated condition is a lipid and lipoprotein disorder such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In some embodiments, the FXR mediated condition is a disease where the combined lipid lowering, anti-cholestatic and anti-fibrotic effects of FXR-targeted medicaments can be exploited for the treatment of liver steatosis and associated syndromes such as Non-Alcoholic Steatohepatitis (NASH), or for the treatment of cholestatic and fibrotic effects that are associated with alcohol-induced cirrhosis, or with viral-borne forms of hepatitis.

In conjunction with the hypolipidemic effects it was shown that loss of functional FXR leads to increased atherosclerosis in ApoE knockout mice. Accordingly, FXR agonists can have clinical utility as anti-atherosclerotic and cardioprotective drugs. The downregulation of Endothelin-1 in Vascular Smooth Muscle Cells can also contribute to such beneficial therapeutic effects.

In some embodiments, the FXR mediated condition is a cardiovascular disorder, such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells. Thus, FXR can be a potential target for the treatment of proliferative diseases, especially metastasizing cancer forms that express a small molecule responsive form of FXR.

In some embodiments, the FXR mediated condition is a malignant hyperproliferative disorder such as different forms of cancer, specifically certain forms of breast, liver or colon cancer where interference with an FXR ligand will have a beneficial impact.

FXR may be involved in the control of antibacterial defense in the intestine. FXR agonists can have a beneficial impact in the therapy of Inflammatory Bowel Disorders (IBD). For example, in IBD forms where the upper (ileal) part of the intestine is affected (e.g., ileal Crohn's disease).

FXR agonists could have beneficial effects through FXR mediated control of bacterial growth. In IBD, the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

In some embodiments, the FXR mediated condition is a disease related to an Inflammatory Bowel Disease, such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

In some embodiments, the FXR mediated condition is obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In some embodiments, the FXR mediated condition is a clinical complication of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of diabetes are also encompassed by the present disclosure.

In some embodiments, the FXR mediated condition is a condition and disease which result from chronic fatty and fibrotic degeneration of organs due to enforced lipid and specifically triglyceride accumulation and subsequent activation of profibrotic pathways. Such conditions and diseases encompass NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system.

In a some embodiments, the FXR mediated condition is congenital hepatic fibrosis.

In some embodiments for the methods described herein, the patient is suffering from an FXR mediated condition selected from:

- a chronic intrahepatic or extrahepatic cholestatic condition;
- liver fibrosis;
- a chronic or obstructive inflammatory disorder of the liver;
- liver cirrhosis;
- liver steatosis or an associated syndrome;
- a cholestatic or fibrotic effect that is associated with alcohol-induced cirrhosis or with a viral-borne form of hepatitis;
- acute or chronic liver failure;
- liver ischemia after major liver resection;
- chemotherapy associated steatohepatitis (CASH);
- a neoplastic disease of the gastrointestinal tract or liver;
- an Inflammatory Bowel Disease (IBD);
- a lipid disorder or lipoprotein disorder;
- Type I Diabetes;
- Type II Diabetes;
- clinical complications of Type I and Type II Diabetes selected from the group consisting of diabetic nephropathy, diabetic neuropathy, diabetic retinopathy, and other observed effects of clinically manifest long term Diabetes;
- Non-Alcoholic Fatty Liver Disease (NAFLD);
- Non-Alcoholic Steatohepatitis (NASH);
- obesity;
- a metabolic syndrome selected from the group consisting of combined conditions of dyslipidemia, diabetes, and abnormally high body-mass index;
- acute myocardial infarction;
- acute stroke;
- thrombosis that occurs as an endpoint of chronic obstructive atherosclerosis;
- a non-malignant hyperproliferative disorder;
- a malignant hyperproliferative disorder selected from the group consisting of hepatocellular carcinoma, colon adenoma, and polyposis;
- colon adenocarcinoma;
- breast cancer;
- pancreas adenocarcinoma;
- Barrett's esophagus;
- kidney disease selected from diabetic kidney disease or chronic kidney disease;
- adrenal gland disorder selected from adrenal insufficiency and congenital adrenal hyperplasia; and
- a cholestatic disease selected from the group consisting of Primary Biliary Cirrhosis (PBC), Primary Sclerosing Cholangitis (PSC), and intrahepatic cholestasis of pregnancy.

In some embodiments, the patient is suffering from liver disease, inflammatory bowel disease (IBD), Crohn's disease, or ulcerative colitis.

In some embodiments, the patient is suffering from a Hepatitis B infection. In some embodiments, the patient is suffering from Hepatitis B virus (HBV)-related liver cirrhosis.

In some embodiments, the patient is suffering from non-alcoholic steatohepatitis (NASH), primary biliary cholangitis (PBC), or primary sclerosing cholangitis (PSC).

In some embodiments, the patient is suffering from NASH. In some embodiments, the patient is suffering from PBC. In some embodiments, the patient is suffering from PSC.

FXR Agonists

Exemplary FXR agonists for use in the methods described herein are as follows. Specific FXR agonists as well as methods for preparing FXR agonists as described herein can be found in WO 2013/007387, WO 2017/218330, and WO 2020/150136, which publications are hereby incorporated by reference in their entirety.

In some embodiments, the FXR agonist is a compound of Formula (TA), an enantiomer, diastereomer, tautomer, solvate, prodrug or pharmaceutical acceptable salt thereof (1A)

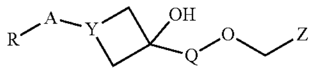

wherein

R is selected from the group consisting of $COOR_6$, $CONR_7R_8$, tetrazolyl, $SO_2NR_7R_8$, $C_{1-6}$ alkyl, $SO_2$—$C_{1-6}$ alkyl and H, with $R_6$ independently selected from the group consisting of H or $C_{1-6}$ alkyl, and $R_7$ and $R_8$ independently from each other selected from the group consisting of H, $C_{1-6}$ alkyl, halo-$C_{1-6}$ alkyl, $C_{1-6}$ alkylene-$R_9$, $SO_2$—$C_{1-6}$ alkyl, wherein $R_9$ is selected from the group consisting of COOH, OH and $SO_3H$;

A is selected from the group consisting of phenyl, pyridyl, pyrimidyl, pyrazolyl, indolyl, thienyl, benzothienyl, indazolyl, benzisoxazolyl, benzofuranyl, benzotriazolyl, furanyl, benzothiazolyl, thiazolyl, oxadiazolyl, each optionally substituted with one or two groups independently selected from the group consisting of OH, O—$C_{1-6}$ alkyl, O-halo-$C_{1-6}$ alkyl, $C_{1-6}$ alkyl, halo-$C_{1-6}$ alkyl, $C_{3-6}$ cycloalkyl and halogen;

Q is selected from the group consisting of phenyl, pyridyl, thiazolyl, thiophenyl, pyrimidyl, each optionally substituted with one or two groups independently selected from the group consisting of $C_{1-6}$ alkyl, halo-$C_{1-6}$ alkyl, halogen and $CF_3$;

Y is selected from N or CH;

Z is selected from

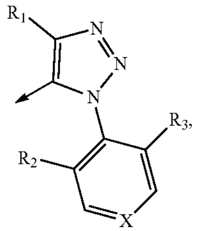

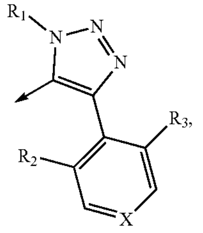

-continued

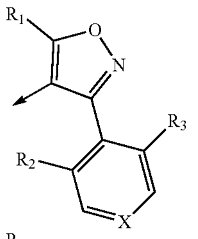

or

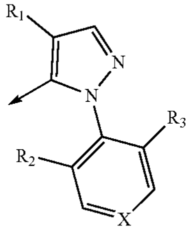

wherein

X=CH, N, NO;

$R_1$ is selected from the group consisting of hydrogen, $C_{1-3}$ alkyl, $C_{3-6}$ cycloalkyl, $C_{4-5}$ alkylcycloalkyl, wherein $C_{1-3}$ alkyl is optionally substituted with 1 to 3 substituents independently selected from halogen, hydroxy or $C_{1-6}$ alkoxy; and $R_2$ and $R_3$ are independently selected from the group consisting of hydrogen, $C_{1-3}$ alkyl, $C_{1-3}$ haloalkyl, $C_{1-3}$ alkoxy, $C_{1-3}$ haloalkoxy and halogen.

In some embodiments, the FXR agonist is a compound of Formula (1B):

(1B)

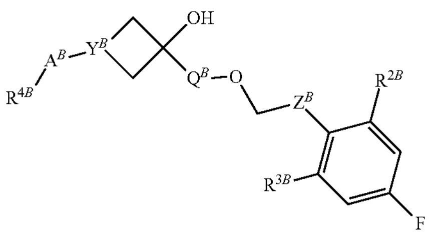

or a pharmaceutically acceptable salt, a stereoisomer, a mixture of stereoisomers, or a tautomer thereof, wherein:

$Q^B$ is phenylene or pyridylene, each of which is optionally substituted with one or two substituents independently selected from halogen, methyl, $C_{1-4}$-alkoxy, halo-$C_{1-4}$-alkoxy, $—CH_2F$, $—CHF_2$, and $—CF_3$;

$Y^B$ is N or CH;

$A^B$ is pyridylene or phenylene, each of which is optionally substituted with one or two groups independently selected from halogen, $C_{1-4}$-alkoxy, halo-$C_{1-4}$-alkoxy, $C_{1-4}$-alkyl, and halo-$C_{1-4}$-alkyl;

$Z^B$ is isoxazole substituted with $R^{1B}$ or pyrazole substituted with $R^{1B}$;

$R^{1B}$ is $C_{1-4}$-alkyl or $C_{3-6}$-cycloalkyl, wherein said $C_{1-4}$-alkyl is optionally substituted with 1 to 3 substituents independently selected from fluoro, hydroxyl, $C_{1-3}$-alkoxy, and fluoro-$C_{1-3}$-alkoxy, and said $C_{3-6}$-cycloalkyl is optionally substituted with 1 to 3 substituents independently selected from fluoro, hydroxyl, $C_{1-3}$-alkyl, fluoro-$C_{1-3}$-alkyl, $C_{1-3}$-alkoxy, and fluoro-$C_{1-3}$-alkoxy;

$R^{2B}$ and $R^{3B}$ are independently selected from hydrogen, halogen, methoxy, $—CF_3$, $—CHF_2$, $—CH_2F$, $—OCH_2F$, $—OCHF_2$, $—OCF_3$, and methyl;

$R^{4B}$ is $—CO_2R^{5B}$ or $—C(O)NR^{5B}R^{6B}$;

$R^{5B}$ is hydrogen, $C_{1-6}$-alkyl, or halo-$C_{1-6}$-alkyl; and $R^{6B}$ is hydrogen or $C_{1-6}$-alkyl, wherein said $C_{1-6}$-alkyl is optionally substituted with 1 to 6 substituents independently selected from halogen, $—SO_3H$, and $—CO_2H$.

In some embodiments, the FXR agonists include, but are not limited to, those described in US2014221659, US2020281911, and WO2020185685.

In some embodiments, the FXR agonist is AGN-242266, AGN-242256, ASC-42, EDP-297 (EP-024297), RDX-023, BWL-200, AKN-083, EDP-305, GNF-5120, cilofexor tromethamine (GS-9674), HPG-1860, IOT-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266, HPD-001, or alendronate.

In some embodiments, the FXR agonist is tropifexor (LJN452), idufexor (LMB-763), AGN-242266, AGN-242256, ASC-42, EDP-297 (EP-024297), RDX-023, BWL-200, AKN-083, EDP-305, GNF-5120, cilofexor tromethamine (GS-9674), HPG-1860, IOT-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266, HPD-001, alendronate,

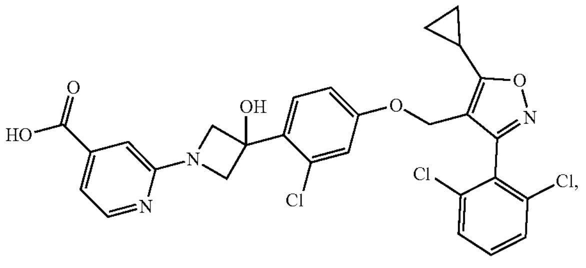 [SMILES: O=C(O)c1ccnc(N2CC(O)(c3ccc(OCc4c(-c5c(Cl)cccc5Cl)noc4C4CC4)cc3Cl)C2)c1]

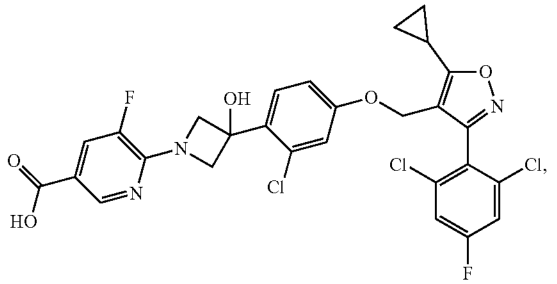

or

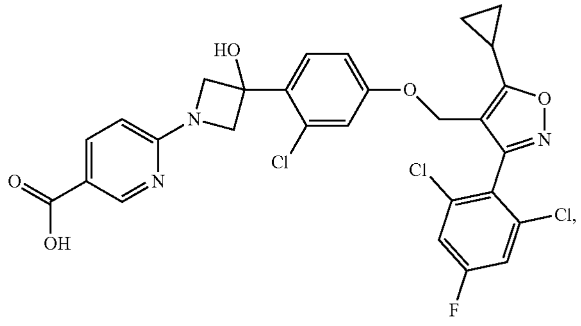

or a pharmaceutically acceptable salt thereof.

In some embodiments, the FXR agonist is:

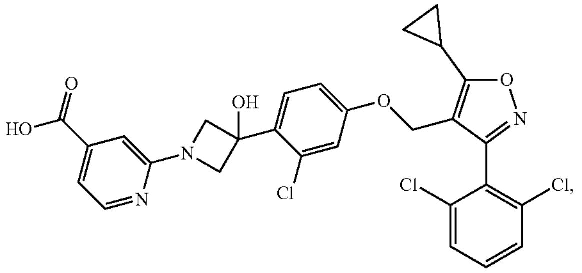

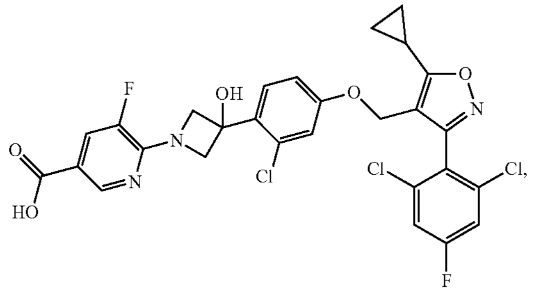

or

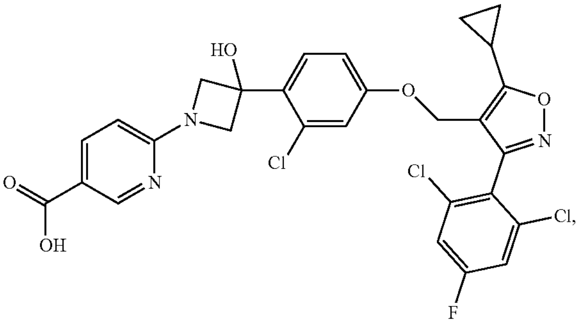

or a pharmaceutically acceptable salt thereof.

In some embodiments, the FXR agonist is:

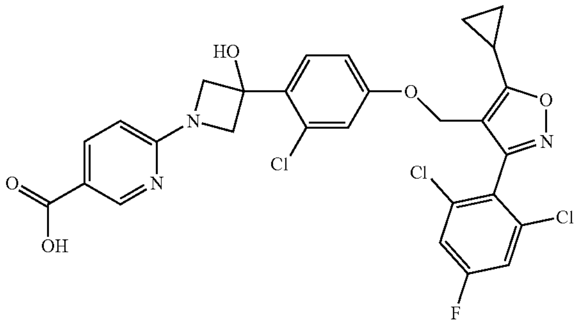 [SMILES: O=C(O)c1ccc(N2CC(O)(c3ccc(OCc4c(-c5c(Cl)cc(F)cc5Cl)noc4C4CC4)cc3Cl)C2)nc1]

or a pharmaceutically acceptable salt thereof.

In some embodiments, the FXR agonist is:

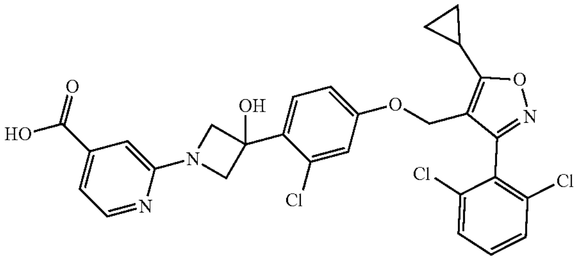 [SMILES: O=C(O)c1ccnc(N2CC(O)(c3ccc(OCc4c(-c5c(Cl)cccc5Cl)noc4C4CC4)cc3Cl)C2)c1]

or a pharmaceutically acceptable salt thereof.

In some embodiments, the FXR agonist is

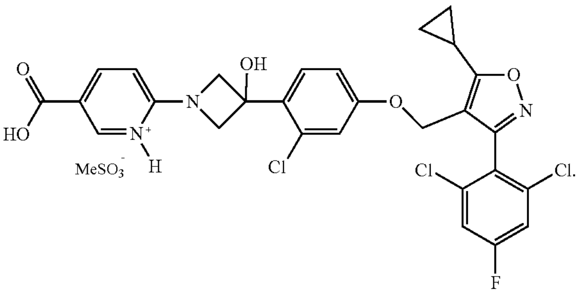

In some embodiments, the FXR agonist is cilofexor.

Also included are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

Compositions provided herein can include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

A composition comprising a mixture of enantiomers (or diastereomers) of a compound described herein or a pharmaceutically acceptable salt thereof, is also provided herein. In some embodiments, the composition comprises a single enantiomer of the compound and is substantially free of the other enantiomer. In certain embodiments, the compound of Formula 1A or 1B (or another Formula as described herein) contains one or more additional stereogenic atom(s) (e.g., at $R^1$ and/or $R^3$). In such instances, the composition may contain a mixture of diastereomers. In some embodiments, the composition comprises a single enantiomer of the compound and is substantially free (i.e., having less than or about 40%, 30%, 25%, 20%, 15%, 10%, 5%, 1%, 0.05%, or 0.01%) of one or more diastereomers.

In certain embodiments, provided are also chelates, noncovalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

In certain embodiments of the methods described herein, the FXR agonist is administered in combination with one or more additional therapeutic agents. In certain embodiments, the one or more additional therapeutic agents is administered prior to, subsequently to, or concurrently with the FXR agonist. In certain embodiments, the FXR agonist is administered in a single composition, formulation, or unit dosage form which further comprises one or more additional therapeutic agents.

In certain embodiments of the methods described herein, the FXR agonist is administered in combination with an effective amount of an ACC inhibitor. Exemplary ACC inhibitors for use in the methods disclosed herein can be found in U.S. Pat. No. 9,453,026 and WO 2021/030142.

In certain embodiments, the ACC inhibitor is a compound of Formula IA:

IA

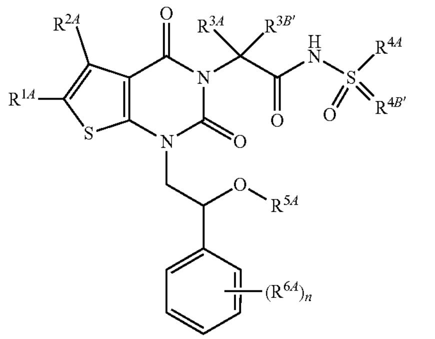

or a pharmaceutically acceptable salt thereof, wherein:

$R^{1A}$ is cyano, halogen, —R', —OR', —SR', —N(R')$_2$, —N(R')C(O)R', —C(O)N(R')$_2$, —N(R')C(O)N(R')$_2$, —N(R')C(O)OR', —OC(O)N(R')$_2$, —N(R')SO$_2$R', —SO$_2$N(R')$_2$, —C(O)R', —C(O)OR', —OC(O)R', —S(O)R', —SO$_2$R', or a cyclic group selected from a 4-8 membered monocyclic heterocycle having 1-2 heteroatoms independently selected from nitrogen, oxygen, or sulfur, a 5-6 membered monocyclic heteroaryl having 1-4 heteroatoms independently selected from nitrogen, oxygen, or sulfur, or a 8-10 membered bicyclic heteroaryl having 1-5 heteroatoms independently selected from nitrogen, oxygen, or sulfur, wherein each cyclic group is independently optionally substituted with 1-4 substituents independently selected from halogen, cyano, $C_{1-3}$ alkyl, and $C_{1-3}$ alkoxy;

$R^{2A}$ is hydrogen or $C_{1-4}$ alkyl, optionally substituted with one or more halogen, —OR', —SR', —N(R')$_2$, —N(R')C(O)R', —C(O)N(R')$_2$, —N(R')C(O)N(R')$_2$, —N(R')C(O)OR', —OC(O)N(R')$_2$, —N(R')SO$_2$R', —SO$_2$N(R')$_2$, —C(O)R', —C(O)OR', —OC(O)R', —S(O)R', or —SO$_2$R';

each R' is independently hydrogen or a group selected from $C_{1-6}$ alkyl, 3-8 membered monocyclic cycloalkyl, phenyl, 8-10 membered bicyclic aryl, 4-8 membered monocyclic heteroaryl having 1-2 heteroatoms independently selected from nitrogen, oxygen, or sulfur, 5-6 membered monocyclic heteroaryl having 1-4 heteroatoms independently selected from nitrogen, oxygen, or sulfur, and 8-10 membered bicyclic heteroaryl having 1-5 heteroatoms independently selected from nitrogen, oxygen, or sulfur, wherein each group is optionally substituted with 1-4 substituents independently selected from halogen, cyano, $C_{1-3}$ alkyl, and $C_{1-3}$ alkoxy;

$R^{3A}$ and $R^{3B'}$ are each independently hydrogen or a $C_{1-3}$ alkyl optionally substituted with 1 to 3 substituents independently selected from halogen, cyano, $C_{1-3}$ alkyl, or $C_{1-3}$ alkoxy; or $R^{3A}$ and $R^{3B'}$ together with the carbon to which they are attached form cyclopropylenyl, cyclobutylenyl, oxetanyl, or tetrahydrofuranyl, each optionally substituted with 1 to 3 substituents independently selected from halogen, cyano, $C_{1-3}$ alkyl, or $C_{1-3}$ alkoxy;

$R^{4A}$ is $C_{1-6}$ alkyl, $C_{1-6}$ alkoxy, $C_{3-6}$ cycloalkyl, $C_{3-6}$ cycloalkoxy, phenyl, or phenoxy, each optionally substituted with 1 to 3 substituents independently selected from halogen, cyano, $C_{1-3}$ alkyl, $C_{1-6}$ alkoxy, $C_{3-6}$ cycloalkyl, or $C_{3-6}$ cycloalkoxy, wherein each $C_{1-3}$ alkyl, $C_{1-6}$ alkoxy, $C_{3-6}$ cycloalkyl, or $C_{3-6}$ cycloalkoxy is optionally substituted with one $C_{1-3}$ alkoxy or 1 to 3 halogens; or $R^{4A}$ is —OR$^{41}$, wherein $R^{41}$ is a 5-6 membered heteroaryl having 1-2, heteroatoms independently selected from nitrogen, oxygen, or sulfur, optionally substituted with 1 to 3 substituents independently selected from halogen, cyano, or $C_{1-3}$ alkyl; or $R^{4A}$ is —N($R^{42}$)$_2$, wherein each $R^{42}$ is independently selected from hydrogen, $C_{1-6}$ alkyl, or $C_{3-6}$ cycloalkyl; or two $R^{42}$ together with the nitrogen to which they are attached to form a 4-6 membered heterocycle, optionally substituted with one $C_{1-3}$ alkoxy or 1 to 3 halogens;

$R^{4B'}$ is oxo or =NR$^{43}$, wherein $R^{43}$ is $C_{1-6}$ alkyl, $C_{3-6}$ cycloalkyl, $C_{4-6}$ heterocyclyl, $C_{3-6}$ cycloalkoxy, phenyl, or 5-6 membered heteroaryl having 1-2 heteroatoms independently selected from nitrogen, oxygen, or sulfur, wherein each $R^{43}$ is optionally substituted with 1 to 3 substituents independently selected from halogen, cyano, or $C_{1-3}$ alkyl;

$R^{5A}$ is an 6-12 membered fused, bridged, or spiro heterocycle having 1 or 2 heteroatoms independently selected from oxygen, sulfur, or nitrogen, wherein the fused, bridged, or spiro heterocycle is optionally substituted with 1 to 4 substituents independently selected from halogen, hydroxyl, oxo, amino, cyano, —OR$^{51}$, —SR$^{51}$, —N($R^{51}$)$_2$, —N($R^{51}$)C(O)R$^{51}$, —C(O)N($R^{51}$)$_2$, —N($R^{51}$)C(O)N($R^{51}$)$_2$, —N($R^{51}$)C(O)OR$^{51}$, —OC(O)N($R^{51}$)$_2$, —N($R^{51}$)SO$_2$R$^{51}$, —SO$_2$N($R^{51}$)$_2$, —C(O)R$^{51}$, —C(O)OR$^{51}$, —OC(O)R$^{51}$, —S(O)R$^{51}$, or —SO$_2$R, $C_{1-3}$ alkyl, and $C_{1-3}$ alkoxy, wherein each $R^{51}$ is independently hydrogen or $C_{1-3}$ alkyl;

$R^{6A}$ is hydrogen, halogen $C_{1-3}$ alkyl, $C_{1-6}$ alkoxy, $C_{3-6}$ cycloalkyl, or $C_{3-6}$ cycloalkoxy, wherein the $C_{1-3}$ alkyl, $C_{1-6}$ alkoxy, $C_{3-6}$ cycloalkyl, or $C_{3-6}$ cycloalkoxy is optionally substituted with one —O—CH$_3$ or 1 to 3 halogens; and n is 1, 2, or 3.

Exemplary ACC inhibitors include 4-(4-[(1-isopropyl-7-oxo-1,4,6,7-tetrahydro-1'H-spiro[indazole-5,4'-piperidin]-1'-yl)carbonyl]-6-methoxypyridin-2-yl)benzoic acid or firsocostat (GS-0976, see e.g., U.S. Pat. No. 9,453,026), or a pharmaceutically acceptable salt thereof.

In certain embodiments, the ACC inhibitor is:

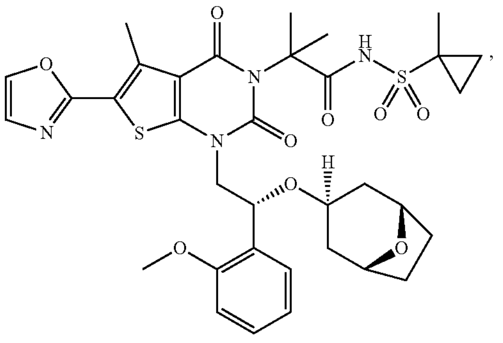 [SMILES: COc1ccccc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2]

or a pharmaceutically acceptable salt thereof.

In certain embodiments, the ACC inhibitor is:

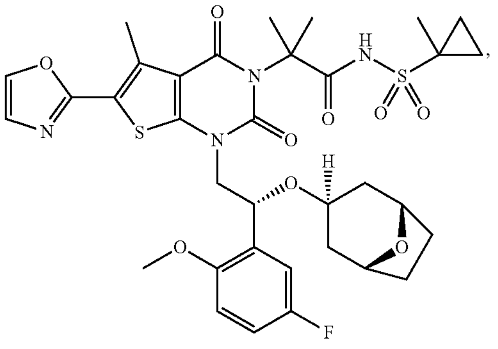 [SMILES: COc1ccc(F)cc1[C@H](Cn1c(=O)n(C(C)(C)C(=O)NS(=O)(=O)C2(C)CC2)c(=O)c2c(C)c(-c3ncco3)sc21)O[C@@H]1C[C@H]2CC[C@@H](C1)O2]

or a pharmaceutically acceptable salt thereof.

In certain embodiments, the ACC inhibitor is:

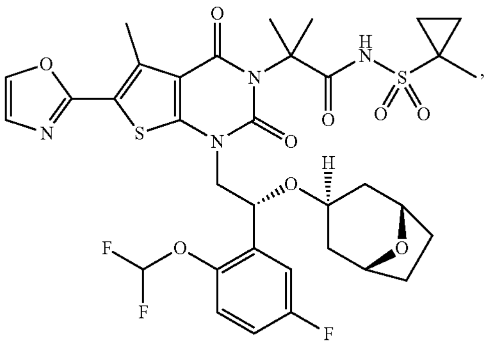 [SMILES: Cc1c(-c2ncco2)sc2c1c(=O)n(C(C)(C)C(=O)NS(=O)(=O)C1(C)CC1)c(=O)n2C[C@H](O[C@@H]1C[C@H]2CC[C@@H](C1)O2)c1cc(F)ccc1OC(F)F]

or a pharmaceutically acceptable salt thereof.

In certain embodiments, the ACC inhibitor is:

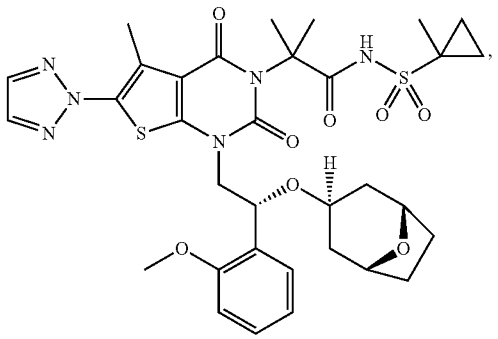 [SMILES: COc1ccccc1[C@H](Cn1c(=O)n(C(C)(C)C(=O)NS(=O)(=O)C2(C)CC2)c(=O)c2c(C)c(-n3nccn3)sc21)O[C@@H]1C[C@H]2CC[C@@H](C1)O2]

or a pharmaceutically acceptable salt thereof.

In certain embodiments, the ACC inhibitor is:

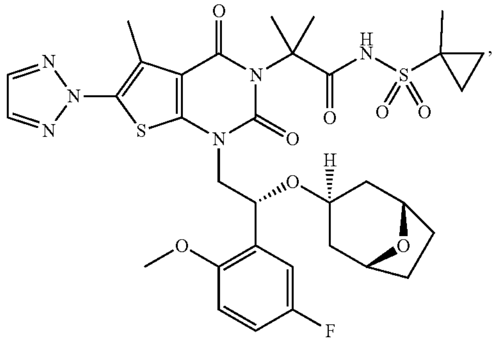 [SMILES: COc1ccc(F)cc1[C@H](Cn1c(=O)n(C(C)(C)C(=O)NS(=O)(=O)C2(C)CC2)c(=O)c2c(C)c(-n3nccn3)sc21)O[C@@H]1C[C@H]2CC[C@@H](C1)O2]

or a pharmaceutically acceptable salt thereof.

In certain embodiments, the ACC inhibitor is:

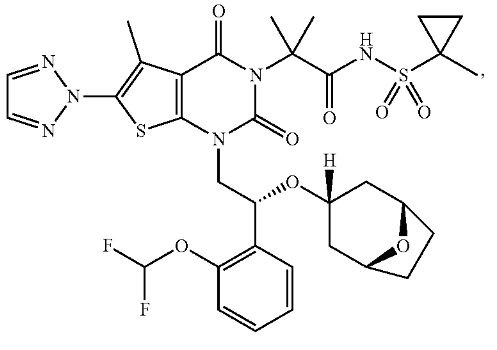 [SMILES: Cc1c(-n2nccn2)sc2c1c(=O)n(C(C)(C)C(=O)NS(=O)(=O)C1(C)CC1)c(=O)n2C[C@H](O[C@H]1C[C@H]2CC[C@@H](C1)O2)c1ccccc1OC(F)F]

or a pharmaceutically acceptable salt thereof.

In certain embodiments, the ACC inhibitor is:

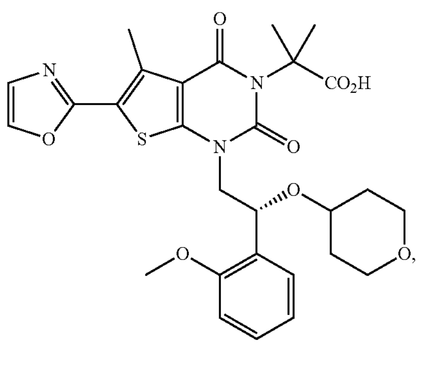 [SMILES: COc1ccccc1[C@H](Cn1c(=O)n(C(C)(C)C(=O)O)c(=O)c2c(C)c(-c3ncco3)sc21)OC1CCOCC1]

or a pharmaceutically acceptable salt thereof.

In certain embodiments, the ACC inhibitor is:

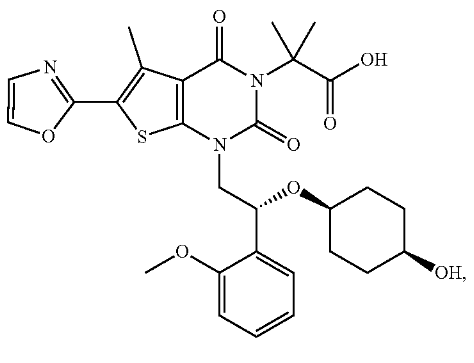 [SMILES: COc1ccccc1[C@H](Cn1c(=O)n(C(C)(C)C(=O)O)c(=O)c2c(C)c(-c3ncco3)sc21)O[C@H]1CC[C@@H](O)CC1]

or a pharmaceutically acceptable salt thereof.

In some embodiments of the methods described herein, the FXR agonist is administered in combination with an effective amount of ASK1 inhibitor. In some embodiments, the ASK1 inhibitor is a compound of Formula:

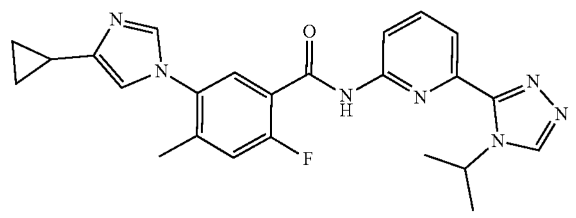 [SMILES: Cc1cc(F)c(C(=O)Nc2cccc(-c3nncn3C(C)C)n2)cc1-n1cnc(C2CC2)c1]

or a pharmaceutically acceptable salt, a stereoisomer, a mixture of stereoisomers, or a tautomer thereof.

ASK1 inhibitors, such as the compound above, can be synthesized and characterized using methods known to those of skill in the art, such as those described in U.S. 2007/0276050 U.S. 2011/0009410, and U.S. 2013/0197037.

In some embodiments of the methods described herein, the FXR agonist is administered in combination with an effective amount of an THR R agonist. In some embodiments, the THR R agonist is a compound of Formula:

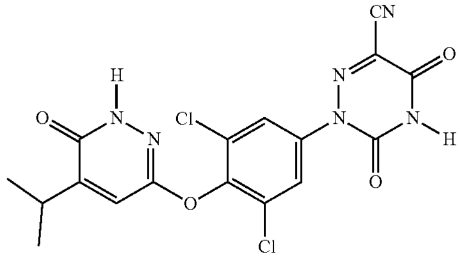 [SMILES: CC(C)c1cc(Oc2c(Cl)cc(-n3nc(C#N)c(=O)[nH]c3=O)cc2Cl)n[nH]c1=O]

or a pharmaceutically acceptable salt, a stereoisomer, a mixture of stereoisomers, or a tautomer thereof.

THR β agonists, such as the above compound, can be synthesized and characterized using methods known to those of skill in the art.

Dosing of an Agent that Inhibits IL-31, an Agent that Inhibits JAK, or the Additional Therapeutic Agents In some embodiments, an agent that inhibits IL-31, or an agent that inhibits JAK, or an optional additional therapeutic agent (such as an FXR agonist or other agents as described herein) is administered in an amount of about 0.1 mg/day to about 1200 mg/day.

In some embodiments, an agent that inhibits IL-31, or an agent that inhibits JAK, or each of the one or more optional additional agent is administered in an amount of 1 mg/day to about 100 mg/day, about 10 mg/day to about 1200 mg/day, about 10 mg/day to about 100 mg/day, about 100 mg/day to about 1200 mg/day, about 400 mg/day to about 1200 mg/day, about 600 mg/day to about 1200 mg/day, about 400 mg/day to about 800 mg/day, or about 600 mg/day to about 800 mg/day. In some embodiments, methods disclosed herein comprise the administration of 0.1 mg/day, 0.5 mg/day, 1 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day or 800 mg/day of an agent that inhibits IL-31, or an agent that inhibits JAK, and optionally a therapeutic agent to a subject in need thereof.

In some embodiments, the total daily dose of an agent that inhibits IL-31, or an agent that inhibits JAK, or each of the one or more additional therapeutic agents (such as an FXR agonist or other agents as described herein) is selected from about 5 mg, about 10 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments, the total daily dose of an agent that inhibits IL-31, or an agent that inhibits JAK, or each of the one or more additional therapeutic agents (such as an FXR agonist or other agents as described herein) is independently between about 5 mg to about 3000 mg, between about 5 mg to about 1000 mg, between about 5 mg to about 500 mg, between about 5 mg to about 100 mg, between about 10 mg to about 3000 mg, between about 10 mg to about 2000 mg, between about 10 mg to about 1000 mg, between about 20 mg to about 1000 mg, between about 30 mg to about 1000 mg, between about 30 mg to about 750 mg, between about 30 mg to about 500 mg, between about 30 mg to about 250 mg, between about 30 mg to about 100 mg, between about 50 mg to about 500 mg, or between about 50 mg to about 100 mg.

Unit Dosage Forms of Additional Therapeutic Agents

In some embodiments, an agent that inhibits IL-31, or an agent that inhibits JAK, and each of the one or more optional additional therapeutic agents (such as an FXR agonist or other agents as described herein) is administered in unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg, or about 100 mg and about 1500 mg of the agent that inhibits IL-31, or the agent that inhibits JAK, or the one or more additional therapeutic agent.

In some embodiments, provided herein are unit dosage formulations comprising about 0.1 mg, 0.25 mg, 0.5 mg, 1 mg, 5 mg, 10 mg, 15 mg, 20 mg, 30 mg, 45 mg, 50 mg, 60 mg, 75 mg, 100 mg, 125 mg, 150 mg, 200 mg, 250 mg, 300 mg, 400 mg, 600 mg or 800 mg of the agent that inhibits IL-31, or the agent that inhibits JAK, or the one or more additional therapeutic agent (such as an FXR agonist or other agents as described herein).

In some embodiments, provided herein are unit dosage formulations that comprise 0.1 mg, 0.25 mg, 0.5 mg, 1 mg, 2.5 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of the agent that inhibits IL-31, or the agent that inhibits JAK, or the one or more additional therapeutic agent (such as an FXR agonist or other agents as described herein).

In some embodiments, provided herein are unit dosage formulations that comprise about 5 mg, about 15 mg, about 20 mg, about 30 mg, about 45 mg, and about 50 mg of the agent that inhibits IL-31, or the agent that inhibits JAK, or the one or more additional therapeutic agent (such as an FXR agonist or other agents as described herein).

Administration of an Agent that Inhibits IL-31 or an Agent that Inhibits JAK or the One or More Additional Therapeutic Agents In some embodiments, provided methods comprise administering a pharmaceutically acceptable composition comprising an agent that inhibits IL-31, and/or an agent that inhibits JAK, and/or the one or more additional therapeutic agent (such as an FXR agonist or other agents as described herein), one, two, three, or four times a day.

In some embodiments, a pharmaceutically acceptable composition comprising an agent that inhibits IL-31 or the one or more additional therapeutic agent is administered once daily ("QD").

In some embodiments, a pharmaceutically acceptable composition comprising an agent that inhibits JAK or the one or more additional therapeutic agent is administered once daily ("QD").

In some embodiments, a pharmaceutically acceptable composition comprising an agent that inhibits IL-31 or the one or more additional therapeutic agent is administered twice daily. In some embodiments, twice daily administration refers to an agent, compound, or composition that is administered "BID," or two equivalent doses administered at two different times in one day.

In some embodiments, a pharmaceutically acceptable composition comprising an agent that inhibits JAK or the one or more additional therapeutic agent is administered twice daily. In some embodiments, twice daily administration refers to an agent, compound, or composition that is administered "BID," or two equivalent doses administered at two different times in one day.

In some embodiments, a pharmaceutically acceptable composition comprising an agent that inhibits IL-31 or one or more additional therapeutic agents is administered three times a day. In some embodiments, a pharmaceutically acceptable composition comprising an agent that inhibits IL-31 or one or more additional therapeutic agents is administered "TID," or three equivalent doses administered at three different times in one day.

In some embodiments, a pharmaceutically acceptable composition comprising an agent that inhibits JAK or one or more additional therapeutic agents is administered three times a day. In some embodiments, a pharmaceutically acceptable composition comprising an agent that inhibits JAK or one or more additional therapeutic agents is administered "TID," or three equivalent doses administered at three different times in one day.

In some embodiments, a pharmaceutically acceptable composition comprising an agent that inhibits IL-31 or one or more additional therapeutic agents is administered four times a day. In some embodiments, a pharmaceutically acceptable composition comprising an agent that inhibits IL-31 or one or more additional therapeutic agents is administered "QID", or four equivalent doses administered at four different times in one day. In some embodiments, a pharmaceutically acceptable composition comprising an agent that inhibits IL-31 or one or more additional therapeutic agents is administered for a various number of days (for example 14, 21, 28) with a various number of days between treatment (0, 14, 21, 28).

In some embodiments, a pharmaceutically acceptable composition comprising an agent that inhibits JAK or one or more additional therapeutic agents is administered four times a day. In some embodiments, a pharmaceutically acceptable composition comprising an agent that inhibits JAK or one or more additional therapeutic agents is administered "QID", or four equivalent doses administered at four different times in one day. In some embodiments, a pharmaceutically acceptable composition comprising an agent that inhibits JAK or one or more additional therapeutic agents is administered for a various number of days (for example 14, 21, 28) with a various number of days between treatment (0, 14, 21, 28).

In some embodiments, an agent that inhibits IL-31 or an additional therapeutic agent is administered orally. In some embodiments, an agent that inhibits JAK or an additional therapeutic agent is administered orally.

An agent that inhibits IL-31, an agent that inhibits JAK, or an additional therapeutic agent can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

Pharmaceutical Compositions and Modes of Administration

Compounds or agents provided herein are usually administered in the form of pharmaceutical compositions. Thus, provided herein are also pharmaceutical compositions that contain one or more of the compounds or agents described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients.

Some embodiments provide for compositions comprising an FXR agonist and a means for inhibiting IL-31 or a means for slowing or preventing an increase in serum IL-31 levels.

Also provided herein are compositions comprising an FXR agonist and a means for inhibiting JAK.

Some embodiments provide for compositions comprising cilofexor and a means for inhibiting IL-31 or a means for slowing or preventing an increase in serum IL-31 levels.

Also provided herein are compositions comprising cilofexor and a means for inhibiting JAK.

Some embodiments provide for compositions comprising an FXR agonist and an agent that inhibits IL-31.

Some embodiments provide for compositions comprising an FXR agonist and an agent that inhibits JAK.

Some embodiments provide for compositions comprising an FXR agonist, an agent that inhibits IL-31, and an agent that inhibits JAK.

Some embodiments provide for compositions comprising cilofexor and an agent that inhibits IL-31.

Some embodiments provide for compositions comprising cilofexor and an agent that inhibits JAK.

Some embodiments provide for compositions comprising cilofexor, an agent that inhibits IL-31, and an agent that inhibits JAK.

Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein (or agent as described herein) or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound or agent described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds or agents described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Further Combination Therapies

In one embodiment, the compounds or argent disclosed herein may be used in combination with one or more additional therapeutic agents. In some embodiments, a compound or agent of the present disclosure, or a pharmaceutically acceptable salt thereof, can be combined with a therapeutically effective amount of one or more (e.g., one, two, three, four, one or two, one to three, or one to four) additional therapeutic agents.

In some embodiments, the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, a TGFβ antagonist, a LPAR antagonist, a SGLT2 inhibitor, a Tpl2 inhibitor, a GLP-1 agonist, or a combination thereof.

The benefit of combination may be increased efficacy and/or reduced side effects for a component as the dose of that component may be adjusted down to reduce its side effects while benefiting from its efficacy augmented by the efficacy of the compound of the present disclosure.

In some embodiments, the therapeutic agent, or combination of therapeutic agents, are a(n) ACE inhibitor, 2-Acylglycerol O-acyltransferase 2 (DGAT2) inhibitor, Acetaldehyde dehydrogenase inhibitor, Acetyl CoA carboxylase inhibitor, Adrenergic receptor agonist, Alstrom syndrome protein 1 (ALMS1)/PKC alpha protein interaction inhibitor, Apelin receptor agonist, Diacylglycerol O acyltransferase 2 inhibitor, Adenosine A3 receptor agonist, Adenosine A3 receptor antagonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Adrenergic receptor antagonist, Androgen receptor agonist, Amylin receptor agonist, Angiotensin II AT-1 receptor antagonist, Apical sodium-dependent bile acid transport inhibitor, Autophagy protein modulator, Autotaxin inhibitors, Axl tyrosine kinase receptor inhibitor, Bax protein stimulator, Beta-catenin inhibitor, Bioactive lipid, Calcitonin agonist, Cannabinoid receptor modulator, Caspase inhibitor, Caspase-3 stimulator, Cathepsin inhibitor, Caveolin 1 inhibitor, CCK receptor antagonist, CCL26 gene inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, CDGSH iron sulfur domain protein modulator, chitinase inhibitor, Chloride channel stimulator, Chitotriosidase 1 inhibitor, CNR1 inhibitor, Connective tissue growth factor ligand inhibitor, COT protein kinase inhibitor, Cyclin D1 inhibitor, Cytochrome P450 7A1 inhibitor, Cytochrome P450 reductase inhibitors, DGAT1/2 inhibitor, Diacylglycerol O acyltransferase 1 inhibitor (DGAT1), Cytochrome P450 2E1 inhibitor (CYP2E1), CXCR3 chemokine antagonist, CXCR4 chemokine antagonist, Dihydroceramide delta 4 desaturase inhibitor, Dihydroorotate dehydrogenase inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, fibroblast activation protein inhibitor, Free fatty acid receptor 1 agonist, Galectin-3 inhibitor, GDNF family receptor alpha like agonist, Glucagon receptor agonist, Glucagon-like peptide 1 agonist, Glucocorticoid receptor antagonist, Glucose 6-phosphate 1-dehydrogenase inhibitor, G-protein coupled bile acid receptor 1 agonist, G-protein coupled receptor-119 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, HSD17B13 gene inhibitor, 5-HT 2a receptor antagonist, Hydrolase inhibitor, Hypoxia inducible factor-2 alpha inhibitor, IL-10 agonist, IL-17 antagonist, IL-22 agonist, Ileal sodium bile acid cotransporter inhibitor, Insulin sensitizer, Insulin ligand agonist, Insulin receptor agonist, integrin modulator, Integrin Antagonist, Integrin alpha-V/beta-1 antagonist, Integrin alpha-V/beta-6 antagonist, intereukin-1 receptor-associated kinase 4 (IRAK4) inhibitor, IL-6 receptor agonist, interleukin 17 ligand inhibitor, Jak2 tyrosine kinase inhibitor, Jun N terminal kinase-1 inhibitor, Kelch like ECH associated protein 1 modulator, Ketohexokinase (KHK) inhibitor, Klotho beta stimulator, Leukotriene A4 hydrolase inhibitor, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, LXR inverse agonists, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21 (miR-21) inhibitor, Mitochondrial uncoupler, Mixed lineage kinase-3 inhibitor, Motile sperm domain protein 2 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), NFE2L2 gene inhibitor, Nicotinic acid receptor 1 agonist, Opioid receptor mu antagonist, P2Y13 purinoceptor stimulator, Nuclear erythroid 2-related factor 2 stimulator, Nuclear receptor modulators, Nuclear transport of transcription factor modulator, P2X7 purinoceptor modulator, PACAP type I receptor agonist, PDE 3 inhibitor, PDE 4 inhibitor, PDE 5 inhibitor, PDGF receptor beta modulator, Phenylalanine hydroxylase stimulator, Phospholipase C inhibitor, Phosphoric diester hydrolase inhibitor, PPAR alpha agonist, PPAR delta agonist, PPAR gamma agonist, Peptidyl-prolyl cis-trans isomerase A inhibitor, PNPLA3 gene inhibitor, PPAR gamma modulator, Protease-activated receptor-2 antagonist, Protein kinase modulator, Protein NOV homolog modulator, PTGS2 gene inhibitor, renin inhibitor, Resistin/CAP1 (adenylyl cyclase associated protein 1) interaction inhibitor, Rho associated protein kinase inhibitor, RNA polymerase inhibitors, S-nitrosoglutathione reductase (GSNOR) enzyme inhibitor, Sodium glucose transporter-2 inhibitor, Sphingolipid delta 4 desaturase DES1 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Taste receptor type 2 agonist, Telomerase stimulator, TERT gene modulator, TGF beta (TGFB1) ligand inhibitor, TNF antagonist, Transforming growth factor R (TGF-0), Transforming growth factor R activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, TLR-9 antagonist, VDR agonist, Vitamin D3 receptor modulators, WNT modulators, YAP/TAZ modulator or a Zonulin inhibitor, and combinations thereof.

Non-limiting examples of the one or more additional therapeutic agents include:

- ACE inhibitors, such as enalapril;
- Acetaldehyde dehydrogenase inhibitors, such as ADX-629;
- Acetyl CoA carboxylase (ACC) inhibitors, such as NDI-010976 (firsocostat), DRM-01, gemcabene, GS-834356, PF-05175157, QLT-091382, PF-05221304;
- Acetyl CoA carboxylase/Diacylglycerol O acyltransferase 2 inhibitors, such as PF-07055341;
- Adenosine receptor agonists, such as CF-102 (namodenoson), CF-101 (piclidenoson), CF-502, CGS21680;
- Adenosine A3 receptor antagonist, such as FM-101;
- Adiponectin receptor agonists, such as ADP-355, ADP-399, ALY668-SR;
- Adrenergic receptor antagonist, such as bromocriptine, phentermine, VI-0521;
- Aldehyde dehydrogenase 2 stimulators, such as FP-045;
- Amylin/calcitonin receptor agonists, such as KBP-042, KBP-089;
- AMP activated protein kinase stimulators, such as C-455, PXL-770, 0-304;
- AMP kinase activators/ATP citrate lyase inhibitors, such as bempedoic acid (ETC-1002, ESP-55016);
- AMP activated protein kinase/Endothelial nitric oxide synthase/NAD-dependent deacetylase sirtuin-1 stimulators, such as NS-0200 (leucine+metformin+sildenafil);
- Androgen receptor agonists, such as LPCN-1144, LPCN-1148, testosterone prodrug;
- Angiotensin II AT-1 receptor antagonists, such as irbesartan; Angiopoietin-related protein-3 inhibitors, such as vupanorsen (IONIS-ANGPTL3-LRx);
- Apelin receptor agonist, such as CB-5064, MBT-2;
- Apical sodium-dependent bile acid transport inhibitors, such as A-3907;
- Autophagy protein modulators, such as A-2906, GM-90194;
- Autotaxin (ectonucleotide pyrophosphatase/phosphodiesterase 2 (NPP2 or ENPP2)) inhibitors, such as FP10.47, PAT-505, PAT-048, GLPG-1690, X-165, PF-8380, TJC-0265, TJC-0316, AM-063, BBT-877;
- Axl tyrosine kinase receptor inhibitors, such as bemcentinib (BGB-324, R-428);
- Bax protein stimulators, such as CBL-514;
- Bioactive lipids, such as DS-102;
- Cannabinoid receptor modulators, such as namacizumab (nimacimab), GWP-42004, REV-200, CRB-4001, INV-101, SCN-002;
- Caspase inhibitors, such as emricasan;
- Pan cathepsin B inhibitors, such as VBY-376;
- Pan cathepsin inhibitors, such as VBY-825;
- CCK receptor antagonist, such as proglumide;
- CCL26 gene inhibitor, such as mosedipimod, KDDF-201410-10;
- CCR2/CCR5 chemokine antagonists, such as BMS-687681, cenicriviroc, maraviroc, CCX-872, leronlimab, WXSH-0213;
- CCR2/CCR5 chemokine antagonists and FXR agonists, such as LJC-242 (tropifexor+cenivriviroc);
- CCR2 chemokine antagonists, such as propagermanium;
- CCR2 chemokine/Angiotensin II AT-1 receptor antagonists, such as DMX-200, DMX-250;
- CCR3 chemokine antagonists, such as bertilimumab;
- CD3 antagonists, such as NI-0401 (foralumab);
- CDGSH iron sulfur domain protein modulators, such as EYP-002;
- Chitinase inhibitor, such as OATD-01;
- Chitotriosidase 1 inhibitors, such as OAT-2068;
- Chloride channel stimulators, such as cobiprostone, and lubiprostone;
- Casein kinase-1 (CK1) delta/epsilon inhibitors, such as PF-05006739;
- Connective tissue growth factor ligand inhibitor, such as PBI-4050;
- COT protein kinase inhibitors, such as GS-4875, GS-5290;
- CXCR4 chemokine antagonists, such as AD-214;
- Cytochrome P450 reductase inhibitors, such as SNP-630;
- Diglyceride acyltransferase 2 (DGAT2) inhibitors, such as IONIS-DGAT2Rx, PF-06865571;
- Diglyceride acyltransferase 1 (DGAT1) inhibitors, such as GSK-3008356;
- Diacylglycerol O acyltransferase 1 (DGAT1)/Cytochrome P450 2E1 inhibitors (CYP2E1), such as SNP-610;
- Dihydroorotate dehydrogenase inhibitor, such as vidofludimus;
- Dipeptidyl peptidase IV inhibitors, such as linagliptin, evogliptin;
- Eotaxin ligand inhibitors, such as bertilimumab, CM-101;

Extracellular matrix protein modulators, such as CNX-024;
Farnesoid X receptor (FXR)/G-protein coupled bile acid receptor 1 (TGR5) agonists, such as INT-767;
Fatty acid synthase inhibitors, such as TVB-2640, FT-8225;
Fibroblast growth factor 19 (rhFGF19)/cytochrome P450 (CYP) 7A1 inhibitors, such as aldafermin (NGM-282);
Fibroblast growth factor 21 (FGF-21) ligand modulators, such as AP-025, BMS-986171, B-1654, BI089-100, BOS-580, Pegbelfermin (BMS-986036), B-1344, NN-9499;
Fibroblast growth factor 21 (FGF-21)/glucagon like peptide 1 (GLP-1) agonists, such as YH-25723 (YH-25724; YH-22241), efruxifermin (AKR-001);
FGF receptor agonists/Klotho beta stimulators, such as BFKB-8488A (RG-7992);
Free fatty acid receptor 1 agonist, such as SCO-267;
Galectin-3 inhibitors, such as belapectin (GR-MD-02), GB-1107 (Gal-300), GB-1211 (Gal-400), IMT-001;
GDNF family receptor alpha like agonist, such as NGM-395;
Glucagon-like peptide 1 (GLP1R) agonists, such as ALT-801, AC-3174, liraglutide, cotadutide (MEDI-0382), SAR-425899, LY-3305677, HM-15211, YH-25723, YH-GLP1, RPC-8844, PB-718, PF-06882961, semaglutide;
Glucagon-like peptide 1 receptor agonist; Oxyntomodulin ligand; Glucagon receptor agonist, such as efinopegdutide;
Gastric inhibitory polypeptide/Glucagon-like peptide-1 (GIP/GLP-1) receptor co-agonist, such as tirzepatide (LY-3298176);
PEGylated long-acting glucagon-like peptide-1/glucagon (GLP-1R/GCGR) receptor dual agonist, such as DD-01;
Glucagon/GLP1-receptor agonist, such as BI-456906, NN-6177;
Glucocorticoid receptor antagonists, such as CORT-118335 (miricorilant);
Glucose 6-phosphate 1-dehydrogenase inhibitors, such as ST001;
Glucokinase stimulator, such as dorzagliatin, sinogliatin (RO-5305552);
G-protein coupled bile acid receptor 1 (TGR5) agonists, such as RDX-009, INT-777, HY-209;
G-protein coupled receptor 84 antagonist, such as PBI-4547;
G-protein coupled receptor-119 agonist, such as DA-1241;
Heat shock protein 47 (HSP47) inhibitors, such as ND-L02-s0201;
Hedgehog protein TGF beta ligand inhibitors, such as Oxy-210;
Histone deacetylase inhibitors/STAT-3 modulators, such as SFX-01;
HMG CoA reductase inhibitors, such as atorvastatin, fluvastatin, pitavastatin, pravastatin, rosuvastatin, simvastatin;
HSD17B13 gene inhibitor, such as ALN-HSD, ARO-HSD;
Hydrolase inhibitor, such as ABD-X;
Hypoxia inducible factor-2 alpha inhibitors, such as PT-2567;
IL-10 agonists, such as peg-ilodecakin;
Ileal sodium bile acid cotransporter inhibitors, such as odevixibat (A-4250), volixibat potassium ethanolate hydrate (SHP-262), GSK2330672, CJ-14199, elobixibat (A-3309);
Insulin sensitizers, such as, KBP-042, azemiglitazone potassium (MSDC-0602K), ION-224, MSDC-5514, Px-102, RG-125 (AZD4076), Tolimidone, VVP-100X, CB-4211, ETI-101;
Insulin ligand/dsInsulin receptor agonists, such as ORMD-0801;
Integrin antagonists, such as IDL-2965;
IL-6 receptor agonists, such as KM-2702;
Integrin alpha-V/beta-6 and alpha-V/beta-1 dual inhibitor; such as PLN-74809;
Interleukin 17 ligand inhibitor, such as netakimab;
Jun N terminal kinase-1 inhibitor, such as CC-90001;
Kelch like ECH associated protein 1 modulator, such as alpha-cyclodextrin-stabilized sulforaphane;
Ketohexokinase (KHK) inhibitors, such as PF-06835919, LY-3478045, LY-3522348;
beta Klotho (KLB)—FGF1c agonists, such as MK-3655 (NGM-313);
Leukotriene A4 hydrolase inhibitor, such as LYS-006;
5-Lipoxygenase inhibitors, such as tipelukast (MN-001), epeleuton (DS-102, (AF-102);
Lipoprotein lipase inhibitors, such as CAT-2003;
LPL gene stimulators, such as alipogene tiparvovec;
Liver X receptor (LXR) inhibitors, such as PX-665, PX-L603, PX-L493, BMS-852927, T-0901317, GW-3965, SR-9238;
Lysophosphatidate-1 receptor antagonists, such as BMT-053011, UD-009 (CP-2090), AR-479, ITMN-10534, BMS-986020, KI-16198, BMS-986278, BMS-986234;
Lysyl oxidase homolog 2 inhibitors, such as simtuzumab, PXS-5382A (PXS-5338);
Macrophage mannose receptor 1 modulators, such as tilmanocept-Cy3 (technetium Tc 99m tilmanocept);
Matrix metalloprotease inhibitors, such as ALS-L1023;
Membrane copper amine oxidase (VAP-1) inhibitors, such as TERN-201, TT-01025;
MEKK-5 protein kinase (ASK-1) inhibitors, such as CJ-16871, CS-17919, selonsertib (GS-4997), SRT-015, GS-444217, GST-HG-151, TERN-301;
MCH receptor-1 antagonists, such as CSTI-100 (ALB-127158);
Semicarbazide-Sensitive Amine Oxidase/Vascular Adhesion Protein-1 (SSAO/VAP-1) Inhibitors, such as PXS-4728A (BI-1467335);
Methionine aminopeptidase-2 inhibitors, such as ZGN-1061, ZGN-839, ZN-1345;
Methyl CpG binding protein 2 modulators, such as mercaptamine;
Mineralocorticoid receptor antagonists (MCRA), such as MT-3995 (apararenone);
Mitochondrial uncouplers, such as 2,4-dinitrophenol, HU6, Mito-99-0053;
Mixed lineage kinase-3 inhibitors, such as URMC-099-C;
Motile sperm domain protein 2 inhibitors, such as VB-601;
Myelin basic protein stimulators, such as olesoxime;
Myeloperoxidase inhibitors, such as PF-06667272, AZM-198;
NADPH oxidase inhibitors, such as GKT-831, GenKyoTex, APX-311, setanaxib;
Nicotinic acid receptor 1 agonists, such as ARI-3037MO;

NACHT LRR PYD domain protein 3 (NLRP3) inhibitors, such as KDDF-201406-03, NBC-6, IFM-514, JT-194 (JT-349);
NFE2L2 gene inhibitor, such as GeRP-amiR-144;
Nuclear transport of transcription factor modulators, such as AMTX-100;
Nuclear receptor modulators, such as DUR-928 (DV-928);
Opioid receptor mu antagonists, such as methylnaltrexone;
P2X7 purinoceptor modulators, such as SGM-1019;
P2Y13 purinoceptor stimulators, such as CER-209;
PDE 3/4 inhibitors, such as tipelukast (MN-001);
PDE 5 inhibitors, such as sildenafil, MSTM-102;
PDGF receptor beta modulators, such as BOT-191, BOT-509;
Peptidyl-prolyl cis-trans isomerase inhibitors, such as CRV-431 (CPI-432-32), NVP-018, NV-556 (NVP-025);
Phenylalanine hydroxylase stimulators, such as HepaStem;
Phosphoric diester hydrolase inhibitor, such as ZSP-1601;
PNPLA3 gene inhibitor, such as AZD-2693;
PPAR agonists, such as Chiglitazar, elafibranor (GFT-505), seladelpar lysine (MBX-8025), deuterated pioglitazone R-enantiomer, pioglitazone, PXL-065 (DRX-065), saroglitazar, lanifibranor (IVA-337), CHS-131, pemafibrate (K-877), ZG-0588, ZSP-0678; ZSYM-008; fenofibrate;
Protease-activated receptor-2 antagonists, such as PZ-235;
Protein kinase modulators, such as CNX-014;
Protein NOV homolog modulators, such as BLR-200;
PTGS2 gene inhibitors, such as STP-705, STP-707;
Renin inhibitors, such as PRO-20;
Resistin/CAP1 (adenylyl cyclase associated protein 1) interaction inhibitors, such as DWJ-211;
Rev protein modulator, such as ABX-464;
Rho associated protein kinase (ROCK) inhibitors, such as REDX-10178 (REDX-10325), KD-025, RXC-007, TDI-01;
RNA polymerase inhibitors, such as rifaximin;
Snitrosoglutathionereductase (GSNOR) enzyme inhibitors, such as SL-891;
Sodium glucose transporter-2 (SGLT2) inhibitors, such as ipragliflozin, remogliflozin etabonate, ertugliflozin, dapagliflozin, tofogliflozin, sotagliflozin;
Sodium glucose transporter-1/2 (SGLT 1/2) inhibitors, such as licogliflozin bis(prolinate) (LIK-066);
SREBP transcription factor inhibitors, such as CAT-2003, HPN-01, MDV-4463;
Stearoyl CoA desaturase-1 inhibitors, such as aramchol;
Taste receptor type 2 agonists, such as ARD-101;
Thyroid hormone receptor beta agonists, such as ALG-009, ASC-41, CNPT-101101; CNPT-101207, CS-27186, KY-41111, resmetirom (MGL-3196), MGL-3745, TERN-501, VK-2809, HP-515;
TLR-2/TLR-4 antagonists, such as VB-201 (CI-201);
TLR-4 antagonists, such as JKB-121, JKB-122, naltrexone;
Tyrosine kinase receptor modulators, such as CNX-025, GFE-2137 (repurposed nitazoxanide);
TLR-9 antagonist, such as GNKS-356, AVO-101;
TNF antagonist, such as ALF-421;
GPCR modulators, such as CNX-023;
Nuclear hormone receptor modulators, such as Px-102;
VDR agonist, such as CK-15;
Xanthine oxidase inhibitors, such as ACQT-1127;
Xanthine oxidase/Urate anion exchanger 1 (URAT1) inhibitors, such as RLBN-1001, RLBN-1127; or
Zonulin Inhibitors, such as larazotide acetate (INN-202).

In certain embodiments, the one or more additional therapeutic agents is an ileal sodium bile acid cotransporter inhibitor, including but not limited to odevixibat (also known as A-4250 or Bylvay).

In certain specific embodiments, the one or more additional therapeutic agents are selected from A-4250, AC-3174, acetylsalicylic acid, AK-20, alipogene tiparvovec, AMX-342, AN-3015, anti-CXCR3 antibodies, anti-TAGE antibody, aramchol, ARI-3037MO, ASP-8232, AXA-1125, bertilimumab, Betaine anhydrous, BI-1467335, BMS-986036, BMS-986171, BMT-053011, BOT-191, BTT-1023, budesonide, BX-003, CAT-2003, cenicriviroc, CBW-511, CER-209, CF-102, CGS21680, CNX-014, CNX-023, CNX-024, CNX-025, cobiprostone, colesevelam, dabigatran etexilate mesylate, dapagliflozin, DCR-LIV1, deuterated pioglitazone R-enantiomer, 2,4-dinitrophenol, DRX-065, DS-102, DUR-928, edaravone (TTYP-01), EDP-305, elafibranor (GFT-505), emricasan, enalapril, ertugliflozin, evogliptin, F-351, fluasterone (ST-002), FT-4101, GDD-3898, GH-509, GKT-831, GNF-5120, GRI-0621, GR-MD-02, GS-300, GS-4997, GS-9674, GS-4875, GS-5290, HEC-96719, HTD-1801, HS-10356, HSG-4112, HST-202, HST-201, HU-6, hydrochlorothiazide, icosabutate (PRC-4016), icosapent ethyl, IMM-124-E, INT-767, INV-240, ION-455, IONIS-DGAT2Rx, ipragliflozin, Irbesarta, propagermanium, IVA-337, J2H-1702, JKB-121, KB-GE-001, KBLP-004, KBLP-009, KBP-042, KD-025, M790, M780, M450, metformin, sildenafil, LB-700, LC-280126, linagliptin, liraglutide, (LJN-452) (tropifexor), LM-011, LM-002 (CVI-LM-002), LMB-763, LYN-100, MB-N-008, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-011, NP-135, NP-160, norursodeoxycholic acid, NV-422, NVP-022, 0-304, obeticholic acid (OCA), 25HC3S, olesoxime, PAT-505, PAT-048, PBI-4547, peg-ilodecakin, pioglitazone, pirfenidone, PRI-724, PX20606, Px-102, PX-L603, PX-L493, PXS-4728A, PZ-235, PZH-2109, RCYM-001, RDX-009, remogliflozin etabonate, RG-125 (AZD4076), RP-005, RPI-500, S-723595, saroglitazar, SBP-301, semaglutide, SH-2442, SHC-028, SHC-023, simtuzumab, solithromycin, sotagliflozin, statins (atorvastatin, fluvastatin, pitavastatin, pravastatin, rosuvastatin, simvastatin), TCM-606F, TEV-45478, TQA-3526, TQA-3563, tipelukast (MN-001), TLY-012, TRX-318, TVB-2640, TXR-611, TXR-612, TS-20004, UD-009, UN-03, ursodeoxycholic acid, VBY-376, VBY-825, VK-2809, vismodegib, volixibat potassium ethanolate hydrate (SHP-626), VVP-100X, WAV-301, WNT-974, WXSH-0038, WXSH-0078, XEN-103, XRx-117, XTYW-003, XW-003, XW-004, XZP-5610, ZGN-839, ZG-5216, ZSYM-008, or ZYSM-007.

Examples of Acetyl CoA carboxylase (ACC) inhibitors include, but are not limited to, those described in US2013123231, US2019134041, US2017267690, and US2018298025;

Examples of Acetyl CoA carboxylase (ACC) inhibitors/Farnesoid X receptor (FXR) agonists include, but are not limited to, those described in US2018280394;

Examples of Acetyl CoA carboxylase (ACC) inhibitors/Farnesoid X receptor (FXR) agonists/MEKK-5 protein kinase (ASK-1) inhibitors include, but are not limited to, those described in US2018021341 and US2018333401;

Examples of Acetyl CoA carboxylase (ACC)/MEKK-5 protein kinase (ASK-1) inhibitors include, but are not limited to, those described in US2018311244;

Examples of Farnesoid X receptor (FXR) agonists/MEKK-5 protein kinase (ASK-1) inhibitors include, but are not limited to those described in US2017273952 and US201813320;

Examples of MEKK-5 protein kinase (ASK-1) inhibitors include, but are not limited to, those described in US2011009410, US2013197037, US2016244430, and US2016280683.

Kits

Provided herein are also kits that include a compound or agent described herein, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound or agent as described herein, or a pharmaceutically acceptable salt, tautomer, stereoisomer, mixture of stereoisomers, prodrug, or deuterated analog thereof, and a label and/or instructions for use of the compounds or agents in the treatment of the indications, including the diseases or conditions, described herein.

Provided herein are also articles of manufacture that include a compound or agent described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: CILO Increased Serum IL-31

CILO Increased IL-31 in NASH Patients

Serum IL-31 (SIMOA©assay; Myriad, Austin, TX) was measured in a Phase 2 study of cilofexor (CILO, a non-steroidal FXR agonist) in non-cirrhotic NASH (n=140) patients. Patients were randomized 2:2:1 to CILO 100 mg, 30 mg, or placebo daily. Associations between serum IL-31 and pruritus-related adverse events and patient-reported outcomes (Visual Analog Scale [VAS] and 5-D Itch) were determined.

Among NASH patients, 8/9 (89%) patients with grade 2-3 pruritus received CILO 100 mg; one patient (1/9, 11%) receiving 30 mg CILO reported grade 2-3 pruritus; and no patients in the placebo group reported grade 2-3 pruritus (Table 1).

TABLE 1

| | CILO 100 mg | CILO 30 mg | Placebo |
|---|---|---|---|
| Grade 1 | 8/56 (14%) | 10/56 (18%) | 5/28 (18%) |
| Grade 2 | 7/56 (13%) | 1/56 (2%) | 0/28 (0%) |
| Grade 3 | 1/56 (2%) | 0/56 (0%) | 0/28 (0%) |
| Any Grade | 16/56 (29%) | 11/56 (20) | 5/28 (18%) |

In NASH patients, CILO increased serum IL-31 in a dose-dependent manner from week 1 (W1) to week 24 (W24) (FIG. 1A). At W24, median (IQR) serum IL-31 levels were 0.26 (0.13, 0.82) pg/mL in the 100 mg group, 0.15 (0.062, 0.27) pg/mL in the 30 mg group (p=0.006 vs. 100 mg), and 0.062 (0.062, 0.12) pg/mL in the placebo group (p<0.001 vs 100 mg) (Table 2).

TABLE 2

| | CILO 100 mg (N = 56) | | CILO 30 mg (N = 56) | | Placebo (N = 28) | |
|---|---|---|---|---|---|---|
| Visit | N | MIQR | N | MIQR | N | MIQR |
| Baseline | 54 | 0.083 (0.062, 0.19) | 56 | 0.09 (0.062, 0.21) | 28 | 0.077 (0.062, 0.105) |
| Week 1 | 54 | 0.21 (0.076, 0.54) | 56 | 0.15 (0.062, 0.28) | 27 | 0.062 (0.062, 0.12) |
| Week 4 | 53 | 0.24 (0.11, 0.67) | 54 | 0.105 (0.062, 0.28) | 27 | 0.074 (0.062, 0.11) |
| Week 8 | 54 | 0.26 (0.12, 0.62) | 53 | 0.14 (0.067, 0.29) | 27 | 0.074 (0.062, 0.11) |
| Week 12 | 53 | 0.26 (0.097, 0.7) | 52 | 0.145 (0.062, 0.245) | 25 | 0.062 (0.062, 0.086) |
| Week 24 | 52 | 0.26 (0.13, 0.815) | 51 | 0.15 (0.062, 0.27) | 24 | 0.062 (0.062, 0.115) |

Figure 1B:
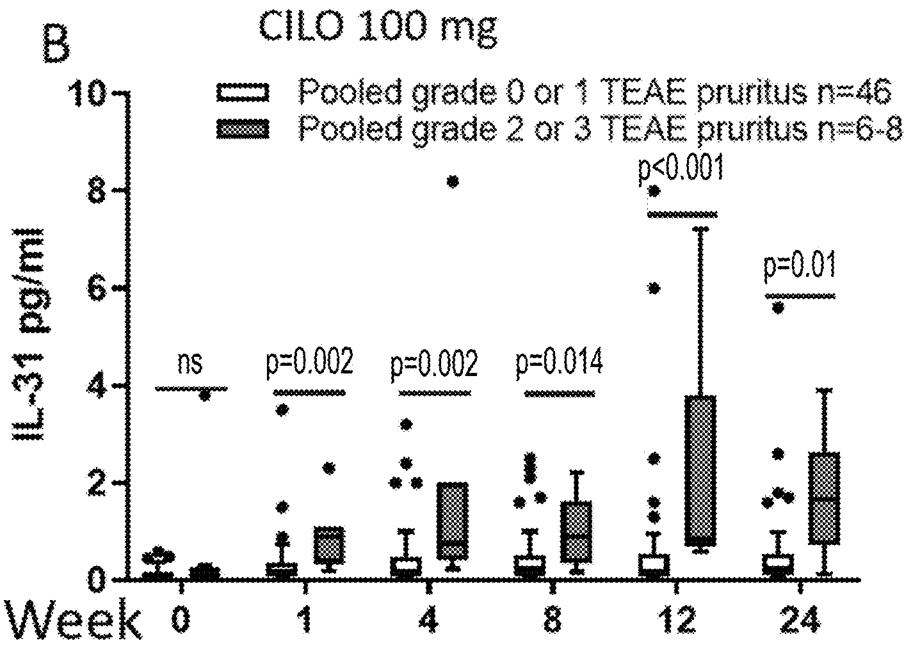

At W24, serum IL-31 levels in patients with grade 2 or 3 pruritus were higher than those with grade 0-1 pruritus on this same dose (1.7 [0.73, 2.6] vs 0.26 [0.12, 0.55] pg/mL; p=0.01 (FIG. 1B). Those with grade 2 or 3 pruritus had more increase of IL-31 than the others at all the post-baseline points at W1 (5.1 fold, p=0.002), W4 (2.9 fold, p=0.002), W8 (3.8 fold, p=0.014), W12 (4.5 fold, P<0.001) and W24 (7 fold, p=0.01)]. While serum IL-31 was weakly correlated with C4 at baseline (BL) (overall ρ=−0.25, p=0.07), changes in IL-31 and C4 from BL to W24 in the CILO 100 mg group were significantly negatively correlated (ρ=−0.46, p<0.001).

The data demonstrates that CILO increased serum IL-31 in NASH patients as well as increased of IL-31 in NASH patients with grade 2 or 3 pruritus, suggesting that FXR agonists cause pruritus associated with increased serum IL-31 levels.

CILO Increased IL-31 in Healthy Subjects

In the CILO phase 1 study, serum IL-31 levels were assessed in pre-dose and post-dose (from 1 to 8 hr) samples from the healthy volunteers (HVs) with placebo or CILO 30 mg, 100 mg or 300 mg. The HVs with CILO 100 mg or 300 mg had elevated serum IL-31 levels with peak concentration at 4-6 hr post-dose samples (data not shown).

Figure 2:
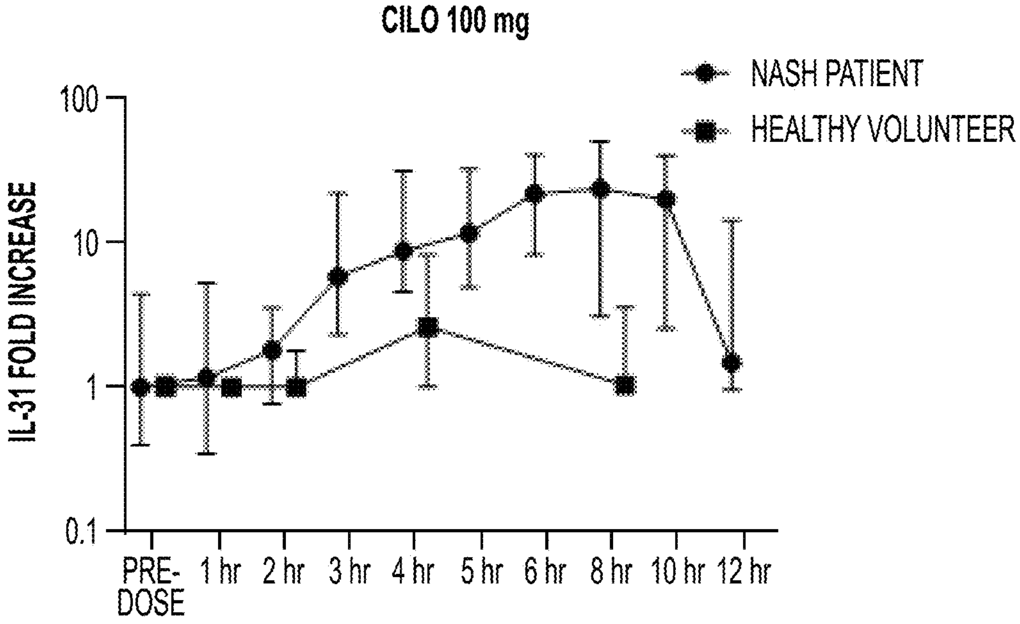
FIG. 2 shows IL-31 increase in a NASH patient as compared to a healthy subject.

A similar intensive sampling study was also performed in the CILO NASH study. IL-31 levels in the serially collected samples were compared in NASH patients and HVs with CILO 100 mg. In HVs with CILO 100 mg, serum IL-31 achieved the peak concentration of 0.22 pg/mL and 2.6 fold increase from pre-dose (data not shown). NASH patients with the same dose had more increased serum IL-31 than HV. The peak concentration in NASH was 13 pg/mL and 23.6 fold (P<0.001 compared to HV) increase from pre-dose (FIG. 2).

Of interest, CILO 100 mg had similar target engagement in HVs and NASH patients as demonstrated by similarly increasing FGF-19 in HV (peak concentration of 591.6 pg/mL at 4 hr post-dose) and NASH patients (peak concentration of 829.7 pg/mL at 4 hr post-dose) (data not shown). NASH patients exhibited higher serum IL-31 levels compared to HVs with CILO 100 mg.

Increased Serum IL-31 in NASH Correlated to Biomarkers of FXR Agonist

Figure 3:
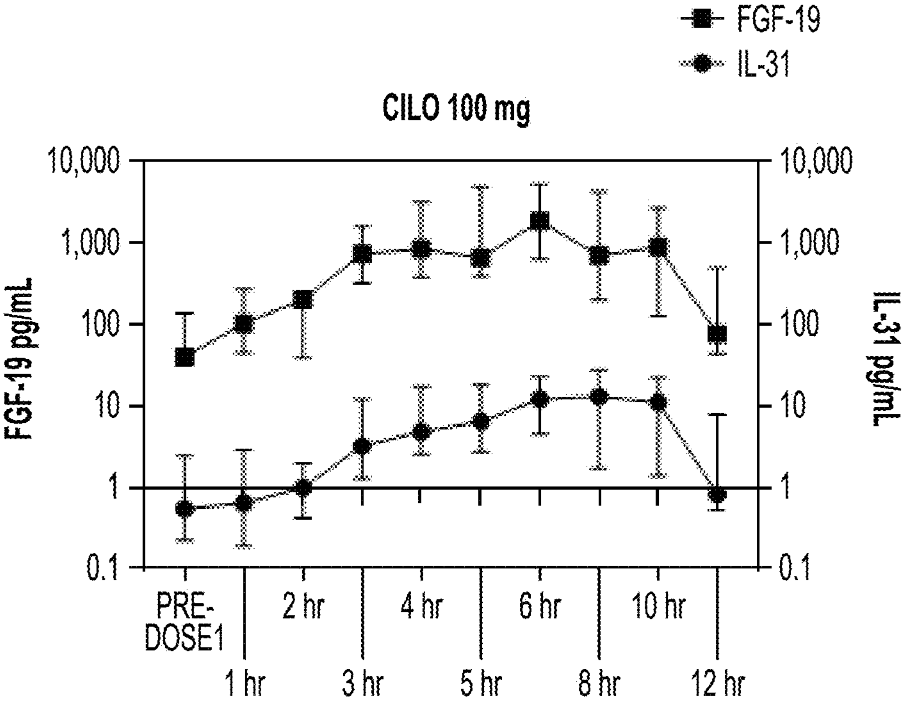
FIG. 3 shows that 100 mg of CILO increased IL-31, which had a temporal correlation with FGF-19.

Activation of FXR in the intestinal epithelial cells induces FGF-19 secretion. FGF-19 suppressed CYP7A1 expression, which is a key enzyme to catalyze 7α-hydroxycholesterol. 7α-hydroxycholesterol is metabolized into 7α-hydroxy-4-cholesten-3-one (C4). The increased FGF-19 and reduced C4 levels in circulation are target engagement assessments for FXR agonists. In the serially collected blood samples, 100 mg CILO increased FGF-19 from median 39.8 pg/mL at pre-dose to the peak concentration around 1826 pg/mL (45.9 fold increase) at 6 hr post-dose. The increase of IL-31 had a temporal correlation with FGF-19 changes with the peak concentration of 12-13 pg/mL at 4-6 hr post-dose (21.8-23.6 fold increase from pre-dose) (FIG. 3). At W24, the C4 levels were significantly declined in both CILO 30 mg and 100 mg groups compared to placebo. While serum IL-31 was weakly correlated with C4 at baseline (BL) (overall $\rho=-0.25$, $p=0.068$), changes in IL-31 and C4 from BL to W24 in the CILO 100 mg group were significantly negatively correlated ($\rho=-0.46$, $p<0.001$), but the correlations in the 30 mg ($\rho=-0.14$, $p=0.33$) or placebo ($\rho=-0.02$, $p=0.93$) groups (Table 3) were not observed.

TABLE 3

| Correlation with IL-31 % Change at W 24 | Placebo (n = 28) | CILO 30 mg (n = 56) | CILO 100 mg (n = 56) |
|---|---|---|---|
| C4, % Change | $\rho = -0.02$ ($p = 0.93$) | $\rho = -0.14$ ($p = 0.33$) | $\rho = -0.46$ ($p < 0.001$) |
| ALP, % Change | $\rho = 0.35$ ($p = 0.1$) | $\rho = 0.35$ ($p = 0.013$) | $\rho = 0.24$ ($p = 0.089$) |

The association of increased IL-31 and FXR PD biomarkers, FGF-19 and C4, suggested an on-target effect of CILO on increased IL-31 levels in NASH patients.

Besides IL-31, several other pruritogens associated with cholestatic itch were evaluated in CILO clinical study, such as primary to secondary BA ratio, lithocholic acid concentration, BA hydrophobicity, and autotaxin. However, none of these reported pruritogens had a significant correlation with VAS or 5-D Itch in NASH or PSC patients (see Example 4)(data not shown).

Example 2: FXR Activation Elevated IL-31 Expression in Hepatocyte

Figure 4A:
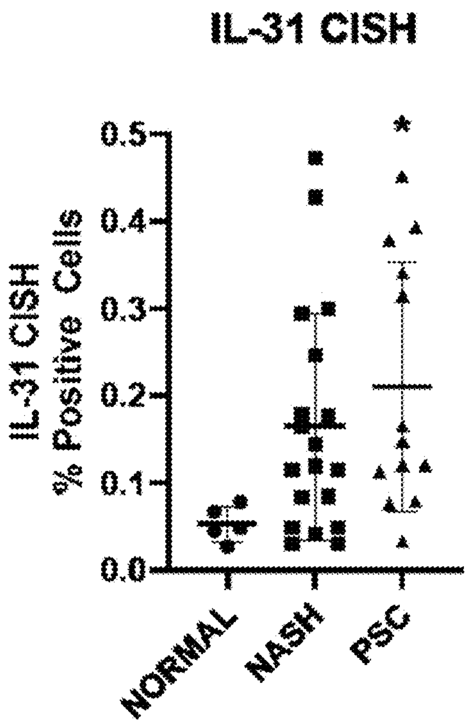
FIG. 4A shows the number of IL-31 positive cells (elevated in the liver biopsy) from 21 NASH (0.16%) and 13 Primary Sclerosing Cholangitis (PSC) (0.21%) patients compared to 5 healthy volunteers.
Figure 4B:
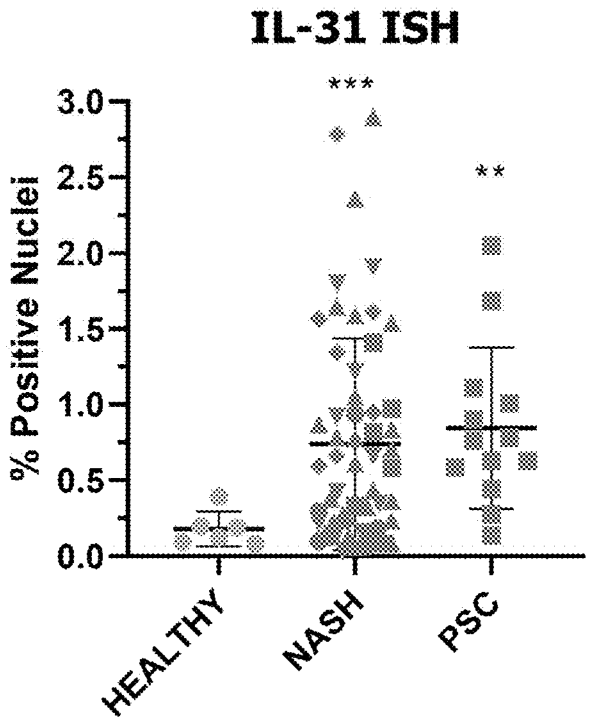
FIG. 4B shows the number of IL-31 positive cells (elevated in the liver biopsy) from 57 NASH and 13 PSC patients compared to 6 healthy volunteers.

The correlation of serum IL-31 and C4 changes in CILO treated NASH patients suggested an association between FXR agonism and IL-31. IL-31 expression in the ileum and liver was investigated by an IL-31 anti-sense probe via in situ hybridization. The number of IL-31 positive cells was elevated in the liver biopsy from NASH (0.16%) and PSC (0.21%) patients compared to HVs (FIG. 4A; see also FIG. 4B) and no IL-31$^+$ cells observed in ileum from HVs or IBD patients. The IL-31$^+$ puncta were found in both non-parenchymal cells and hepatocyte in the liver biopsy from NASH or PSC (data not shown). The IL-31V hepatocytes located at peri-ductal and central vein area and no zonal distribution was observed.

The direct effect of the steroidal FXR agonist, obeticholic acid (OCA, 10 mg/kg QD vs vehicle for 18 days) on serum IL-31 was also assessed in chimeric PXB mice with human hepatocytes, in which human hepatocyte engrafted into mouse liver. The SIMOA® assay was validated to detect human (not murine) IL-31 to distinguish the cellular source.

Figure 5:
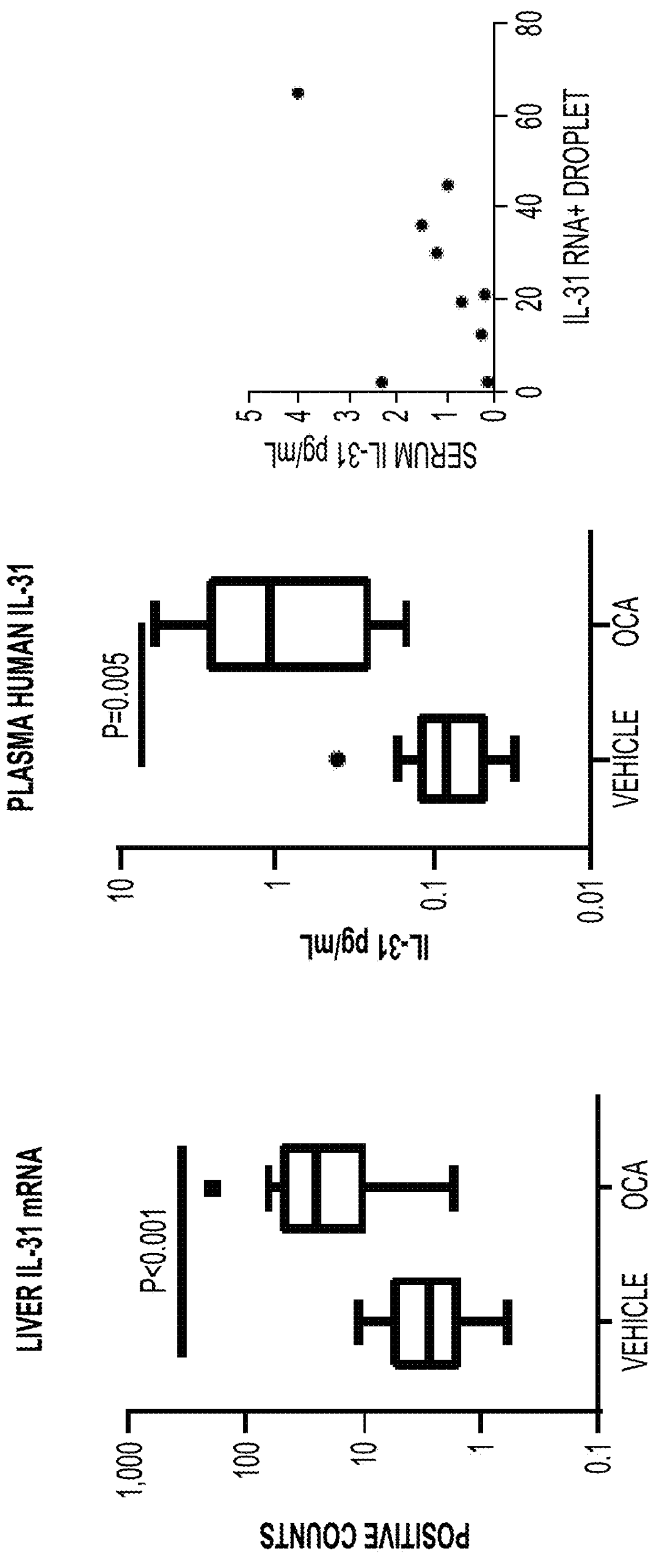
FIG. 5 shows that, in chimeric PXB mice, obeticholic acid (OCA) increased hepatic IL-31 mRNA expression (7.8-fold vs vehicle, $p<0.001$) and serum levels of human IL-31.

In chimeric PXB mice, OCA increased hepatic IL-31 mRNA expression (7.8-fold vs vehicle, p<0.001) and serum levels of human IL-31 (1.1 [0.25, 2.7] vs 0.085 [0.045, 0.13] pg/mL with vehicle, p=0.005) (FIG. 5).

The hepatic IL-31 mRNA correlated to serum IL-31 levels in PXB mice ($\rho=0.61$, $p<0.001$).

The data described herein demonstrates that FXR activation, through agonists or natural ligands (BAs), is associated with increased levels of the pruritogenic cytokine IL-31, which appears to derive in part from increased hepatocyte expression.

Example 3: Increased Serum IL-31 Levels in Patients with Liver Disease

Serum IL-31 was assessed in the specimen collected at day 1 visit (baseline) from five CILO clinical studies on HV and patients with non-cirrhotic NASH, cirrhotic NASH (Cohorts 7 and 8 of the study), PBC, and PSC by ultrasensitive IL-31 SIMOA immunoassay.

Serum IL-31 was not detectible in most HVs. 35/36 (97.2%) of the subjects enrolled in the healthy subject study had serum IL-31 levels under the lower limit of quantification (LLOQ).

Patients with liver disease had increased serum IL-31 levels with median levels from 0.09 to 2.7 pg/mL (FIG. 1A).

In NASH, cirrhotic patients had higher serum IL-31 levels [0.3 (0.2, 0.5) pg/mL] than that in non-cirrhotic patients [0.09 (0.062, 0.16) pg/mL, p<0.001 vs. cirrhotic].

Figure 6:
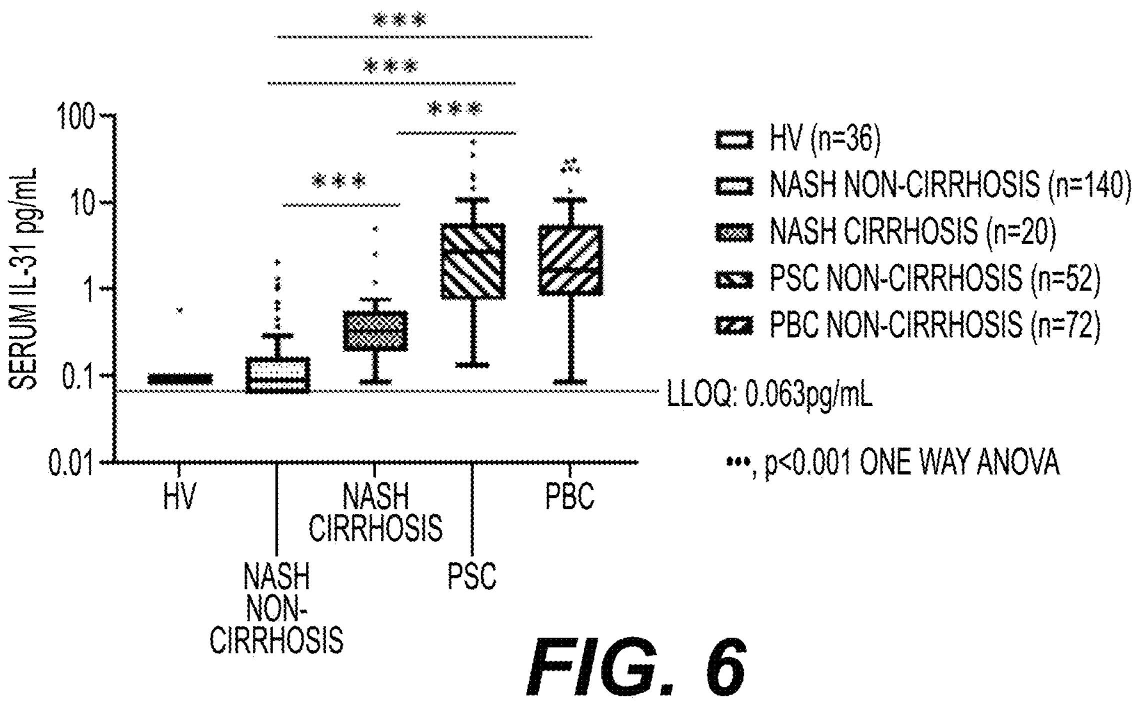
FIG. 6 shows non-cirrhotic Primary Biliary Cirrhosis (PBC) and PSC patients had less liver injury compared to cirrhotic NASH patients but higher serum IL-31 levels.

Of interest, non-cirrhotic PBC and PSC patients had less liver injury compared to cirrhotic NASH patients (lower levels of Child Pugh score, data not shown), but higher serum IL-31 levels [1.7 (0.8, 5.5) pg/mL in PBC and 2.7 (0.8, 5.9) pg/mL in PSC, both p<0.001 vs cirrhotic NASH] (FIG. 6).

Overarching the non-cirrhotic and cirrhotic NASH, PBC and PSC patients, IL-31 levels significantly correlated to serum bile acid (BA) levels with spearman correlation $\rho=0.53$, $p<0.001$, but no significant correlation with other biomarkers of liver injury and fibrosis, like ALT, AST or ELF score (data not shown). This suggested that the increased serum IL-31 in patients with liver disease is a feature of cholestasis associated with elevated serum BA levels.

These studies demonstrate that IL-31 is the putative pruritogen for patients with cholestasis, and BA, a natural ligand of FXR, elevated IL-31 in patients with cholestasis.

Example 4: IL-31 in PSC and PBC Patients

Serum IL-31 (SIMOA® assay; Myriad, Austin, TX) was measured in two Phase 2 studies of cilofexor (CILO, a non-steroidal FXR agonist) in PSC (n=52) and PBC (n=71). In all studies, patients were randomized 2:2:1 to CILO 100 mg, 30 mg, or placebo daily. Associations between serum IL-31 and pruritus-related adverse events and patient-reported outcomes (Visual Analog Scale [VAS] and 5-D Itch) were determined.

Figure 7:
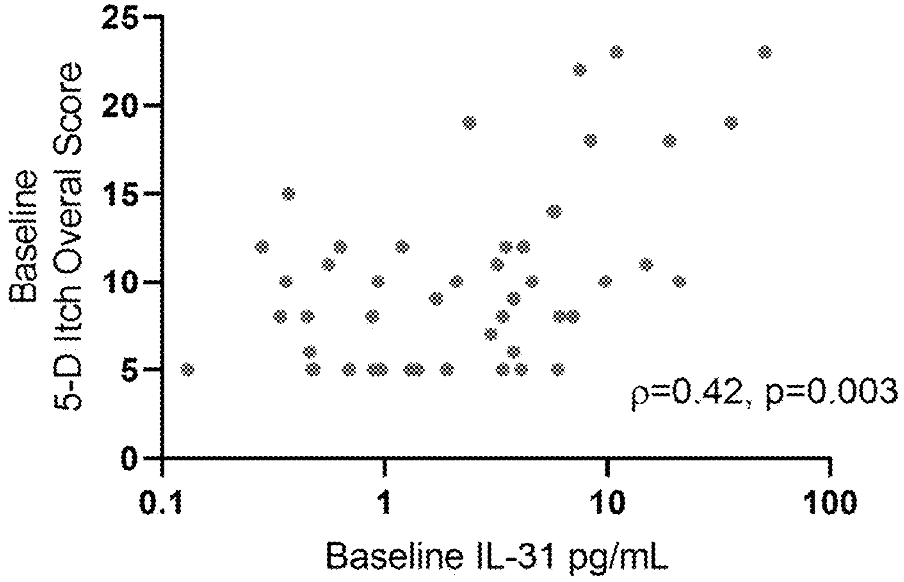
FIG. 7 shows baseline serum IL-31 levels were correlated with 5-D Itch Overall Score in PSC patients.
Figure 8:
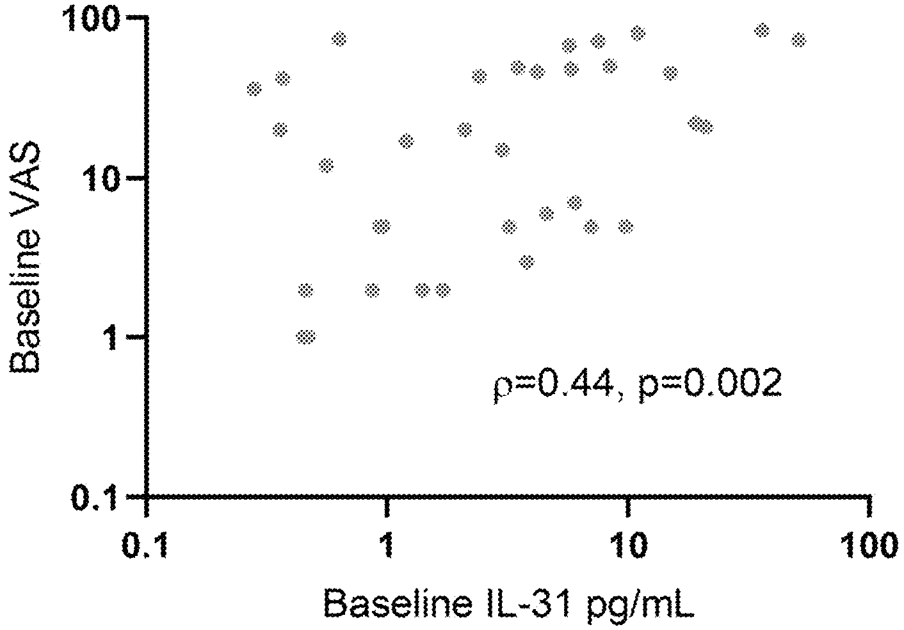
FIG. 8 shows baseline serum IL-31 levels were correlated with Visual Analog Scale (VAS) in PSC patients.

BL serum IL-31 levels were significantly correlated with VAS (ρ=0.42, p=0.003) and 5-D Itch (ρ=0.44, p=0.002) in PSC (Table 4, FIGS. 7 and 8).

TABLE 4

| Serum IL-31 baseline correlation with itch scores or Serum BA | Spearmann Corr. With Serum IL-31 | P-value |
|---|---|---|
| 5D overall score | 0.42 | 0.003 |
| VAS itching score | 0.44 | 0.002 |
| Serum BA | 0.35 | 0.02 |

Figure 9:
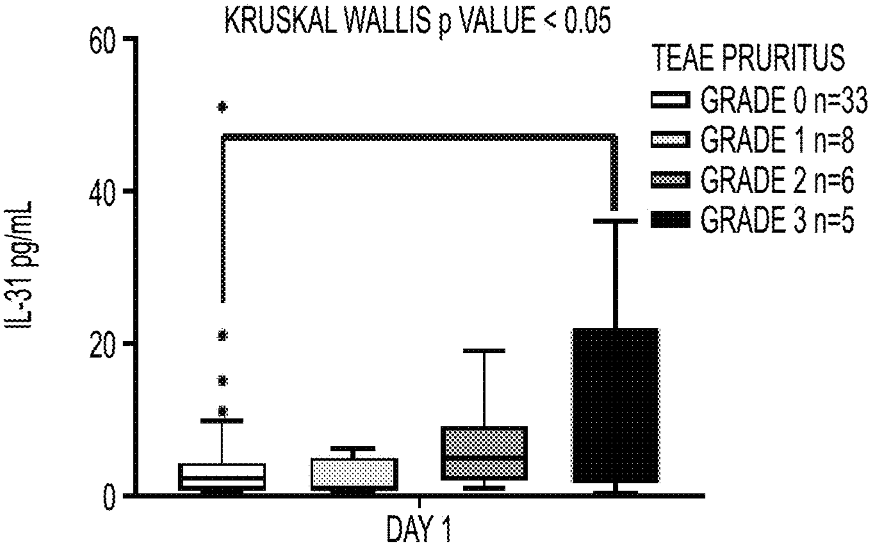
FIG. 9 shows that PSC patients who reported grade 2 or 3 pruritus had elevated serum IL-31 levels compared to grade 0 or 1 patients treated by the same dose of 100 mg CILO.

The PSC patients who reported grade 2 or 3 pruritus during treatment, had elevated baseline serum IL-31 levels compared to grade 0 or 1 patients (FIG. 9). CILO did not exacerbate pruritus in PSC patients. A similar proportion of patients reported grade 2 or 3 pruritus across all the treatment groups (3 subjects receiving 100 mg, 3 subjects receiving 30 mg and 3 subjects receiving placebo) (Table 5).

TABLE 5

| | CILO 100 mg | CILO 30 mg | Placebo |
|---|---|---|---|
| Grade 1 | 5 | 2 | 3 |
| Grade 2 | 1 | 1 | 2 |
| Grade 3 | 2 | 2 | 1 |
| Any Grade | 8 | 5 | 6 |

Figure 10:
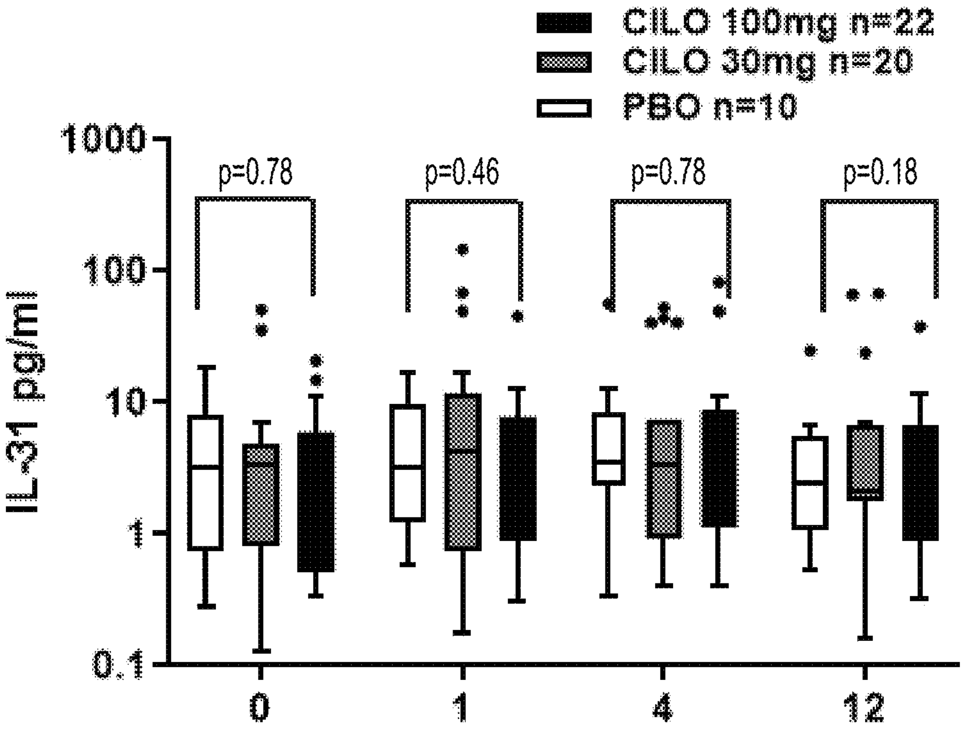
FIG. 10 shows that CILO did not alter serum IL-31 levels during 12-week treatment in PSC patients.

In accordance with the AE pruritus, CILO did not alter the serum IL-31 levels during the 12-week treatment (FIG. 10).

Figure 11:
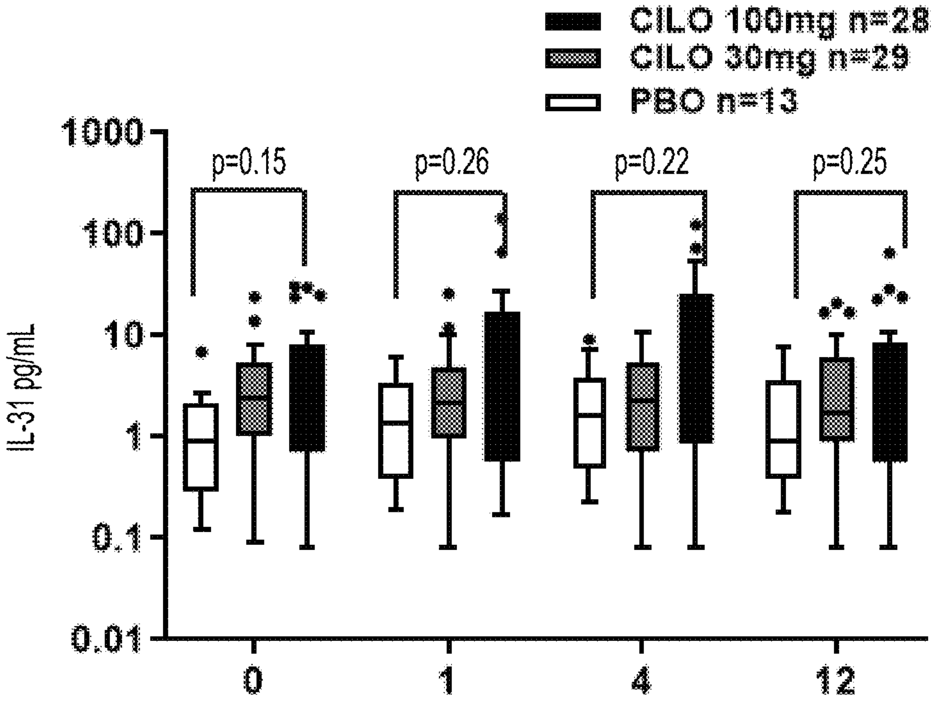
FIG. 11 shows that CILO did not alter serum IL-31 levels during 12-week treatment in PBC patients.

In PBC, IL-31 correlated to VAS (ρ=0.42, p<0.001) and 5-D Itch (ρ=0.58, p<0.001) (Table 6). Compared to the placebo group, CILO did NOT change serum IL-31 levels in fasting samples collected at Weeks 1, 4 and 12 (FIG. 11). However, in the serially collected blood samples post CILO treatment, 100 mg CILO mildly increased IL-31 levels from a median level of 3 pg/mL at pre-dose to 7.4 pg/mL (2.5 fold increase) at 5 hr post-dose.

TABLE 6

| Itching Scores or Serum BA | Spearmann Corr. With Serum IL-31 | P-value |
|---|---|---|
| 5D overall score | 0.48 | <0.001 |
| VAS itching score | 0.39 | <0.001 |
| Serum BA | 0.42 | <0.001 |

In PSC and PBC patients, BL serum IL-31 levels were higher than in NASH (PSC vs PBC vs NASH: 2.7 [0.7, 6.0] vs 1.7 [0.8, 5.5] vs 0.08 [0.062, 0.18] pg/mL; both p<0.001 vs NASH), but a dose-dependent effect of CILO was not observed in PSC or PBC.

Across the patients with NASH, PBC and PSC, the serum IL-31 levels were not associated with severity of liver disease, but serum bile acid (BA) levels.

Thus, it is contemplated that IL-31 is a potential pruritogen for cholestatic itch in PBC and PSC associated with increased serum BA levels. It also was shown that CILO improved cholestasis in PSC and PBC patients by reducing ALP and BA levels. CILO had no effect on serum IL-31 in PSC and PBC.

Example 5: IL-4 in NASH and PSC Patients

Other cellular sources of IL-31 in the NASH and PSC patients treated by CILO were explored.

IL-31 is expressed and secreted by activated T helper 2 (Th2) cell. IL-4, a type II immune cytokine, was associated with activation of Th2 cells and serum IL-31 levels in patients with atopic dermatitis. Serum IL-4 levels were assessed in the CILO NASH and PSC studies.

PSC patients had elevated IL-4 levels compared to NASH patients at BL, but no correlation was observed between serum IL-4 and IL-31 in PSC (data not shown). In NASH, CILO did not elevate serum IL-4 and the changes of IL-31 did not correlate with IL-4 changes in CILO groups at W24 (data not shown).

In murine, FXR is not expressed in T cells, and this study did not support that the FXR agonism elevated IL-31 was derived from activated T cells.

Thus, CILO increased serum IL-31 in NASH without changing other inflammatory markers (IL-4 and IL-18, data not shown).

The invention claimed is:

1. A method of treating pruritus comprising administering to a patient in need thereof an effective amount of an agent that inhibits IL-31, wherein the pruritus is due to the patient being administered an FXR agonist and having increased serum IL-31 levels, wherein the FXR agonist is

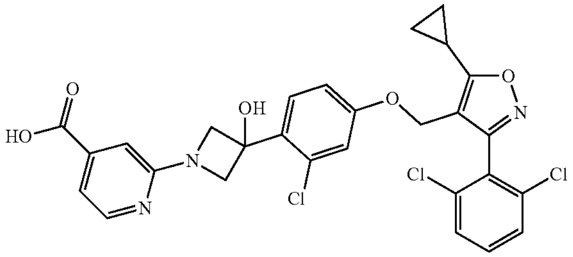 [SMILES: O=C(O)c1ccnc(N2CC(O)(c3ccc(OCc4c(-c5c(Cl)cccc5Cl)noc4C4CC4)cc3Cl)C2)c1]

or a pharmaceutically acceptable salt thereof, and wherein the patient is suffering from non-alcoholic steatohepatitis (NASH).

2. The method of claim 1, wherein the agent that inhibits IL-31 is nemolizumab, BMS-981164, or KPL-716.

3. The method of claim 1, further comprising administering an effective amount of an agent that inhibits janus kinase (JAK).

4. The method of claim 3, wherein the agent that inhibits JAK is selected from: a TYK2 inhibitor, BMS-986165, brepocitinib (PF-06700841), TD-1473, OST-122, BMS-986322, NDI-031301, delgocitinib, fedratinib, peficitinib, panobinostat, izencitinib, momelotinib, deucravacitinib, itacitinib, SHR-0302, deuroxolitinib, ritlecitinib, jaktinib, ARQ-252, pacritinib, CEP-33779, decernotinib, oclacitinib, filgotinib, baricitinib, ruxolitinib, tofacitinib, upadacitinib, abrocitinib, or a pharmaceutically acceptable salt thereof, and a combination thereof.

5. The method of claim 1, wherein the patient is administered the FXR agonist and the agent that inhibits IL-31 sequentially.

6. The method of claim 1, wherein the patient is administered the FXR agonist and the agent that inhibits IL-31 concurrently.

7. The method of claim 1, wherein the patient is administered an FXR agonist prior to administration of the agent that inhibits IL-31.

* * * * *